US007638130B2

(12) United States Patent
Ching et al.

(10) Patent No.: US 7,638,130 B2
(45) Date of Patent: Dec. 29, 2009

(54) **TRUNCATED RECOMBINANT MAJOR OUTER MEMBRANE PROTEIN ANTIGEN (R56) OF *ORIENTIA TSUTSUGAMUSHI* STRAINS KARP, KATO AND GILLIAM AND ITS USE IN ANTIBODY BASED DETECTION ASSAYS AND VACCINES**

(75) Inventors: Wei-Mei Ching, Bethesda, MD (US); Daryl J. Kelly, Newark, OH (US); Gregory A. Dasch, Stone Mountain, GA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 11/964,982

(22) Filed: Dec. 27, 2007

(65) Prior Publication Data

US 2008/0279881 A1 Nov. 13, 2008

Related U.S. Application Data

(60) Division of application No. 10/120,837, filed on Apr. 12, 2002, now Pat. No. 7,335,477, which is a continuation-in-part of application No. 09/218,425, filed on Dec. 22, 1998, now Pat. No. 6,482,415.

(60) Provisional application No. 60/283,373, filed on Apr. 13, 2001, provisional application No. 60/482,415, filed on Dec. 24, 1997.

(51) Int. Cl.
*A61K 39/02* (2006.01)

(52) U.S. Cl. .............. 424/190.1; 424/234.1; 424/184.1; 530/300; 530/350; 530/825; 514/2

(58) Field of Classification Search ....................... None
See application file for complete search history.

(56) References Cited

U.S. PATENT DOCUMENTS 5,439,808 A 8/1995 Blake et al.

FOREIGN PATENT DOCUMENTS

WO WO99/34215 A1 7/1999

OTHER PUBLICATIONS

Ohashi et al (Infect.Immun., 1989, 57(5): 1427-1431).*

Oshahi et al (Gene. 1990. 91: 119-122).*

Stover et al. The 56-kilodalton major protein antigen of *Rickettsia tsutsugamushi*: molecular cloning and sequence analysis of the sta56 gene and precise identification of a strain-specific epitope; 1990. 58(7): 2076-2084.

Kim et al. High-level expression of a 56-kilodalton protein gene (bor56) of *Rickettsia tsutsugamushi* Boryong and its application to enzyme-linked immunosorbent assays. 1993. 31(3):598-605.

Ohashi et al. Purification and partial characterization of a type-specific antigen of *Rickettsia tsutsugamushi*. infect immuno 57(5): 1427-1431.

Ohashi et al. Cloning and sequencing of the gene (tsg56) encoding a type-specific antigen from *Rickettsia tsutsugamushi*. Gene. 1990. 91(1):119-120.

* cited by examiner

*Primary Examiner*—Jennifer E Graser
(74) *Attorney, Agent, or Firm*—Joseph K Hemby, Jr.; Ning Yang; Albert M. Charilla

(57) ABSTRACT

A recombinant, refolded non-fusion polypeptide expressed from a truncated r56 gene of the causative agent of scrub typhus, *Orientia tsutsugamushi* for the Karp, Kato and Gilliam strains has been produced. The invention is useful for detecting prior exposure to scrub typhus, screening for and/or identification of at least one infectious strain-similarity (i.e. a Karp-like, Kato-like or Gilliam-like strain) based on its strength of reaction toward a truncated protein and as a component in vaccine formulation sand production of immune globulins for passive prophylaxis and immunity in subjects.

2 Claims, 7 Drawing Sheets

FIG. .5

SEQUENCE LISTING

```
<160> NUMBER OF SEQ ID NOS: 12

<210> SEQ ID NO 1
<211> LENGTH: 377
<212> TYPE: PRT
<213> ORGANISM: Orientia tsutsugamushi

<400> SEQUENCE: 1

Met Thr Ile Ala Pro Gly Phe Arg Ala Glu Ile Gly Val Met Tyr Leu
1               5                   10                  15

Thr Asn Ile Thr Ala Gln Val Glu Glu Gly Lys Val Lys Ala Asp Ser
20                  25                  30

Val Gly Glu Thr Lys Ala Asp Ser Val Gly Gly Lys Asp Ala Pro Ile
35                  40                  45

Arg Lys Arg Phe Lys Leu Thr Pro Pro Gln Pro Thr Ile Met Pro Ile
50                  55                  60

Ser Ile Ala Asp Arg Asp Phe Gly Ile Asp Ile Pro Asn Ile Pro Gln
```

-continued

```
65                  70                  75                  80

Gln Gln Ala Gln Ala Ala Gln Pro Gln Leu Asn Asp Glu Gln Arg Ala
85                  90                  95

Ala Ala Arg Ile Ala Trp Leu Lys Asn Cys Ala Gly Ile Asp Tyr Arg
100                 105                 110

Val Lys Asn Pro Asn Asp Pro Asn Gly Pro Met Val Ile Asn Pro Ile
115                 120                 125

Leu Leu Asn Ile Pro Gln Gly Asn Pro Asn Pro Val Gly Asn Pro Pro
130                 135                 140

Gln Arg Ala Asn Pro Pro Ala Gly Phe Ala Ile His Asn His Glu Gln
145                 150                 155                 160

Trp Arg His Leu Val Val Gly Leu Ala Ala Leu Ser Asn Ala Asn Lys
165                 170                 175

Pro Ser Ala Ser Pro Val Lys Val Leu Ser Asp Lys Ile Thr Gln Ile
180                 185                 190

Tyr Ser Asp Ile Lys His Leu Ala Asp Ile Ala Gly Ile Asp Val Pro
195                 200                 205

Asp Thr Ser Leu Pro Asn Ser Ala Ser Val Glu Gln Ile Gln Asn Lys
210                 215                 220

Met Gln Glu Leu Asn Asp Leu Leu Glu Glu Leu Arg Glu Ser Phe Asp
225                 230                 235                 240

Gly Tyr Leu Gly Gly Asn Ala Phe Ala Asn Gln Ile Gln Leu Asn Phe
245                 250                 255

Val Met Pro Gln Gln Ala Gln Gln Gln Gly Gln Gly Gln Gln Gln Gln
260                 265                 270

Ala Gln Ala Thr Ala Gln Glu Ala Val Ala Ala Ala Ala Val Arg Leu
275                 280                 285

Ile Asn Gly Asn Asp Gln Ile Ala Gln Leu Tyr Lys Asp Leu Val Lys
290                 295                 300

Leu Gln Arg His Ala Gly Ile Lys Lys Ala Met Glu Lys Leu Ala Ala
305                 310                 315                 320

Gln Gln Glu Glu Asp Ala Lys Asn Gln Gly Glu Gly Asp Cys Lys Gln
325                 330                 335

Gln Gln Gly Thr Ser Glu Lys Ser Lys Lys Gly Lys Asp Lys Glu Ala
340                 345                 350

Glu Phe Asp Leu Ser Met Ile Val Gly Gln Val Lys Leu Tyr Ala Asp
355                 360                 365

Val Met Ile Thr Glu Ser Val Ser Ile
370                 375
```

<210> SEQ ID NO 2
<211> LENGTH: 36
<212> TYPE: DNA
<213> ORGANISM: Orientia tsutsugamushi

<400> SEQUENCE: 2
ttggctgcac atatgacaat cgctccagga tttaga 36

<210> SEQ ID NO 3
<211> LENGTH: 48
<212> TYPE: DNA
<213> ORGANISM: Orientia tsutsugamushi

<400> SEQUENCE: 3
ctttctagaa gtataagcta acccggatcc aacaccagcc tatattga 48

-continued

<210> SEQ ID NO 4
<211> LENGTH: 529
<212> TYPE: PRT
<213> ORGANISM: Orientia tsutsugamushi

<400> SEQUENCE: 4

```
Met Lys Lys Thr Met Leu Ile Ala Ser Ala Met Ser Ala Leu Ser Leu
1               5                   10                  15

Pro Phe Ser Ala Ser Ala Ile Glu Leu Gly Asp Glu Gly Gly Leu Glu
20                  25                  30

Cys Gly Pro Tyr Ala Lys Val Gly Val Val Gly Gly Met Ile Thr Gly
35                  40                  45

Val Glu Ser Thr Arg Leu Asp Pro Ala Asp Ala Gly Gly Lys Lys Gln
50                  55                  60

Leu Pro Leu Thr Thr Ser Met Pro Phe Gly Gly Thr Leu Ala Ala Gly
65                  70                  75                  80

Met Thr Ile Ala Pro Gly Phe Arg Ala Glu Leu Gly Val Met Tyr Leu
85                  90                  95

Ala Asn Val Lys Ala Glu Val Glu Ser Gly Lys Thr Gly Ser Asp Ala
100                 105                 110

Asp Ile Arg Ser Gly Ala Asp Ser Pro Met Pro Gln Arg Tyr Lys Leu
115                 120                 125

Thr Pro Pro Gln Pro Thr Ile Met Pro Ile Ser Ile Ala Asp Arg Asp
130                 135                 140

Leu Gly Val Asp Ile Pro Asn Val Pro Gln Gly Gly Ala Asn His Leu
145                 150                 155                 160

Gly Asp Asn Leu Gly Ala Asn Asp Ile Arg Arg Ala Asp Asp Arg Ile
165                 170                 175

Thr Trp Leu Lys Asn Tyr Ala Gly Val Asp Tyr Met Val Pro Asp Pro
180                 185                 190

Asn Asn Pro Gln Ala Arg Ile Val Asn Pro Val Leu Leu Asn Ile Pro
195                 200                 205

Gln Gly Pro Pro Asn Ala Asn Pro Arg Gln Ala Met Gln Pro Cys Ser
210                 215                 220

Ile Leu Asn Glu Asp His Trp Arg His Leu Val Val Gly Ile Thr Ala
225                 230                 235                 240

Met Ser Asn Ala Asn Lys Pro Ser Val Ser Pro Ile Lys Val Leu Ser
245                 250                 255

Glu Lys Ile Val Gln Ile Tyr Arg Asp Val Lys Pro Phe Ala Arg Val
260                 265                 270

Ala Gly Ile Glu Val Pro Ser Asp Pro Leu Pro Asn Ser Ala Ser Val
275                 280                 285

Glu Gln Ile Gln Asn Lys Met Gln Glu Leu Asn Asp Ile Leu Asp Glu
290                 295                 300

Ile Arg Asp Ser Phe Asp Gly Cys Ile Gly Gly Asn Ala Phe Ala Asn
305                 310                 315                 320

Gln Ile Gln Leu Asn Phe Arg Ile Pro Gln Ala Gln Gln Gln Gly Gln
325                 330                 335

Gly Gln Gln Gln Gln Gln Ala Gln Ala Thr Ala Gln Glu Ala Ala Ala
340                 345                 350

Ala Ala Ala Val Arg Val Leu Asn Asn Asn Asp Gln Ile Ile Lys Leu
355                 360                 365

Tyr Lys Asp Leu Val Lys Leu Lys Arg His Ala Gly Ile Lys Lys Ala
370                 375                 380
```

-continued

```
Met Glu Glu Leu Ala Ala Gln Asp Gly Gly Cys Asn Gly Gly Gly Asp
385                 390                 395                 400

Asn Lys Lys Lys Arg Gly Ala Ser Glu Asp Ser Asp Ala Gly Gly Ala
405                 410                 415

Ser Lys Gly Gly Lys Gly Lys Glu Thr Lys Glu Thr Glu Phe Asp Leu
420                 425                 430

Ser Met Ile Val Gly Gln Val Lys Leu Tyr Ala Asp Leu Phe Thr Thr
435                 440                 445

Glu Ser Phe Ser Ile Tyr Ala Gly Leu Gly Ala Gly Leu Ala Tyr Thr
450                 455                 460

Ser Gly Lys Ile Asp Gly Val Asp Ile Lys Ala Asn Thr Gly Met Val
465                 470                 475                 480

Ala Ser Gly Ala Leu Gly Val Ala Ile Asn Ala Ala Glu Gly Val Tyr
485                 490                 495

Val Asp Thr Glu Gly Ser Tyr Met His Ser Phe Ser Lys Ile Glu Glu
500                 505                 510

Lys Tyr Ser Ile Asn Pro Leu Met Ala Ser Phe Gly Val Arg Tyr Asn
515                 520                 525

Phe


<210> SEQ ID NO 5
<211> LENGTH: 524
<212> TYPE: PRT
<213> ORGANISM: Orientia tsutsugamushi

<400> SEQUENCE: 5

Met Lys Lys Ile Met Leu Ile Ala Ser Ala Met Ser Ala Leu Ser Leu
1               5                   10                  15

Pro Phe Ser Ala Ser Ala Ile Glu Leu Gly Glu Glu Gly Gly Leu Glu
20                  25                  30

Cys Gly Pro Tyr Gly Lys Val Gly Ile Val Gly Gly Met Ile Thr Gly
35                  40                  45

Ala Glu Ser Thr Arg Leu Asp Ser Thr Asp Ser Glu Gly Lys Lys His
50                  55                  60

Leu Ser Leu Thr Thr Gly Leu Pro Phe Gly Gly Thr Leu Ala Ala Gly
65                  70                  75                  80

Met Thr Ile Ala Pro Gly Phe Arg Ala Glu Leu Gly Val Met Tyr Leu
85                  90                  95

Arg Asn Ile Ser Ala Glu Val Glu Val Gly Lys Gly Lys Val Asp Ser
100                 105                 110

Lys Gly Glu Ile Lys Ala Asp Ser Gly Gly Gly Thr Asp Thr Pro Ile
115                 120                 125

Arg Lys Arg Phe Lys Leu Thr Pro Pro Gln Pro Thr Ile Met Pro Ile
130                 135                 140

Ser Ile Ala Asp Arg Asp Val Gly Val Asp Thr Asp Ile Leu Ala Gln
145                 150                 155                 160

Ala Ala Ala Gly Gln Pro Gln Leu Thr Val Glu Gln Arg Ala Ala Asp
165                 170                 175

Arg Ile Ala Trp Leu Lys Asn Tyr Ala Gly Ile Asp Tyr Met Val Pro
180                 185                 190

Asp Pro Gln Asn Pro Asn Ala Arg Val Ile Asn Pro Val Leu Leu Asn
195                 200                 205

Ile Thr Gln Gly Pro Pro Asn Val Gln Pro Arg Pro Arg Gln Asn Leu
210                 215                 220
```

-continued

Asp Ile Leu Asp His Gly Gln Trp Arg His Leu Val Val Gly Val Thr
225 230 235 240

Ala Leu Ser His Ala Asn Lys Pro Ser Val Thr Pro Val Lys Val Leu
245 250 255

Ser Asp Lys Ile Thr Lys Ile Tyr Ser Asp Ile Lys Pro Phe Ala Asp
260 265 270

Ile Ala Gly Ile Asp Val Pro Asp Thr Gly Leu Pro Asn Ser Ala Ser
275 280 285

Val Glu Gln Ile Gln Ser Lys Met Gln Glu Leu Asn Asp Val Leu Glu
290 295 300

Asp Leu Arg Asp Ser Phe Asp Gly Tyr Met Gly Asn Ala Phe Ala Asn
305 310 315 320

Gln Ile Gln Leu Asn Phe Val Met Pro Gln Gln Ala Gln Gln Gln Gln
325 330 335

Gly Gln Gly Gln Gln Gln Gln Ala Gln Ala Thr Ala Gln Glu Ala Val
340 345 350

Ala Ala Ala Ala Val Arg Leu Leu Asn Gly Asn Asp Gln Ile Ala Gln
355 360 365

Leu Tyr Lys Asp Leu Val Lys Leu Gln Arg His Ala Gly Val Lys Lys
370 375 380

Ala Met Glu Lys Leu Ala Ala Gln Gln Glu Glu Asp Ala Lys Asn Gln
385 390 395 400

Gly Glu Gly Asp Cys Lys Gln Gln Gln Gly Ala Ser Glu Lys Ser Lys
405 410 415

Glu Gly Lys Gly Lys Glu Thr Glu Phe Asp Leu Ser Met Ile Val Gly
420 425 430

Gln Val Lys Leu Tyr Ala Asp Leu Phe Thr Thr Glu Ser Phe Ser Ile
435 440 445

Tyr Ala Gly Val Gly Ala Gly Leu Ala His Thr Tyr Gly Lys Ile Asp
450 455 460

Asp Lys Asp Ile Lys Gly His Thr Gly Met Val Ala Ser Gly Ala Leu
465 470 475 480

Gly Val Ala Ile Asn Ala Ala Glu Gly Val Tyr Val Asp Leu Glu Gly
485 490 495

Ser Tyr Met His Ser Phe Ser Lys Ile Glu Glu Lys Tyr Ser Ile Asn
500 505 510

Pro Leu Met Ala Ser Val Gly Val Arg Tyr Asn Phe
515 520

<210> SEQ ID NO 6
<211> LENGTH: 36
<212> TYPE: DNA
<213> ORGANISM: Orientia tsutsugamushi

<400> SEQUENCE: 6
ttagctgcgc atatgacaat tgcaccagga tttaga 36

<210> SEQ ID NO 7
<211> LENGTH: 36
<212> TYPE: DNA
<213> ORGANISM: Orientia tsutsugamushi

<400> SEQUENCE: 7
atgagctaac ccggatccaa caccagccta tattga 36

-continued

<210> SEQ ID NO 8
<211> LENGTH: 36
<212> TYPE: DNA
<213> ORGANISM: Orientia tsutsugamushi
<400> SEQUENCE: 8
ttagctgcac atatgacaat cgcgccagga tttaga 36

<210> SEQ ID NO 9
<211> LENGTH: 36
<212> TYPE: DNA
<213> ORGANISM: Orientia tsutusgamushi
<400> SEQUENCE: 9
ataagctaac ccggatccaa gaccagccta tattga 36

<210> SEQ ID NO 10
<211> LENGTH: 1596
<212> TYPE: DNA
<213> ORGANISM: Orientia tsutsugamushi
<400> SEQUENCE: 10
atgaaaaaaa ttatgttaat tgctagtgca atgtctgcgt tgtcgttgcc attttcagct 60
agtgcaatag aattggggga agaaggatta gagtgtggtc cttatgctaa agttggagtt 120
gttggaggaa tgattactgg cgtagaatct gctcgcttgg atccagctga tgctgaaggc 180
aaaaaacact tgtcattaac aaatgggctg ccatttggtg gaacgttggc tgcaggtatg 240
acaatcgctc caggatttag agcagagata ggtgttatgt accttacaaa tataactgct 300
caggttgaag aaggtaaagt taaggcagat tctgtaggtg agacaaaggc agattctgta 360
ggtgggaaag atgctcctat acgtaagcgg tttaaactta cacctcctca gcctactata 420
atgcctataa gtatagctgt acgtgacttt gggattgata ttcctaacca gacctcagca 480
gcaagcacaa gccgcagcct caggcttaat gatgagcaac gtgctgcagc taggatcgct 540
tggttaaaga attgtgctgg tattgactat agggtaaaaa accctaatga tcctaatggg 600
cctatggtta taaatccgat attgttaaat attccacagg gtaaccctaa tcctgttgga 660
aatccaccgc agcgagcaaa tccgcctgca ggttttgcga tacataacca tgagcaatgg 720
aggcatttgg tagttgggct tgctgcatta tcaaatgcta ataaacctag cgcttctcct 780
gtcaaagtat taagtgataa aattactcag atatatagtg atataaagca tttggctgat 840
atagctggta ttgatgttcc tgatactagt ttgcctaata gtgcatctgt cgaacagata 900
cagaataaaa tgcaagaatt aaacgatcta ttggaagagc tcagagaatc ttttgatggg 960
tatcttggtg gtaatgcttt tgctaatcag atacagttga attttgtcat gccgcagcaa 1020
gcacagcagc aggggcaagg gcagcaacag caagctcaag ctacagcgca agaagcagta 1080
gcagcagcag ctgttaggct tttaaatggc aatgatcaga ttgcgcagtt atataaagat 1140
cttgttaaat tgcagcgtca tgcaggaatt aagaaagcga tggaaaaatt agctgcccaa 1200
caagaagaag atgcaaagaa tcaaggtgaa ggtgactgca agcagcaaca aggaacatct 1260
gaaaaatcta aaaaaggaaa agacaaagag gcagagtttg atctgagtat gattgtcggc 1320
caagttaaac tctatgctga cgtaatgata actgaatcag tctcaatata tgctggtgtt 1380
ggtgcagggt tagcttatac ttctggaaaa atagataata aggatattaa agggcataca 1440
ggcatggttg catcaggagc acttggtgta gcaattaatg ctgctgaagg tgtgtatgtg 1500
gacatagaag gtagttatat gtactcattc agtaaaatag aagagaagta ttcaataaat 1560

-continued

```
cctcttatgg caagtgtaag tgtacgctat aacttc                              1596


<210> SEQ ID NO 11
<211> LENGTH: 1587
<212> TYPE: DNA
<213> ORGANISM: Orientia tsutsugamushi

<400> SEQUENCE: 11

atgaaaaaaa ttatgttaat tgctagtgca atgtctgcat tgtcattgcc gttttcagct      60

agtgcgatag aattggggga tgaaggagga ttagagtgtg gtccttatgc taaagttgga     120

gtcgttggag gaatgattac tggcgtagaa tctactcgct tggatccagc tgatgctggt     180

ggcaaaaaac aattgccatt aacaacctcg atgccatttg gtggtacatt agctgcaggt     240

atgacaatcg cgccaggatt tagagcagag ctaggggtta tgtaccttgc gaatgtaaaa     300

gcagaggtgg aatcaggtaa aactggctct gatgctgata ttagatctgg tgcagattct     360

cctatgcctc agcggtataa acttacacca cctcagccta ctataatgcc tataagtatt     420

gcggatcgtg accttggggt tgatattcct aacgtacctc aaggaggagc taatcacctg     480

ggtgataacc ttggtgctaa tgatattcgg cgtgctgacg ataggatcac ttggttgaag     540

aattatgctg gtgttgacta tatggttcca gatcctaata atcctcaggc tagaattgta     600

aatccagtgc tattaaatat tcctcaaggt ccgcctaatg caaatcctag acaagctatg     660

caaccttgta gtatacttaa ccatgatcac tggaggcatc ttgtagttgg tattactgca     720

atgtcaaatg ctaataaacc tagcgtttct cctatcaaag tattaagtga aaaaattgtc     780

cagatatatc gtgatgtgaa gccgtttgct agagtagctg gtattgaagt tcctagtgat     840

cctttgccta atagtgcatc tgttgagcag atacagaata aaatgcaaga attaaatgat     900

atattggatg agatcagaga ttcttttgac gggtgtattg gtggtaatgc tttcgctaat     960

cagatacagt tgaattttcg cattccgcaa gcacagcagc aggggcaagg gcagcaacag    1020

cagcaagctc aagctacagc gcaagaagca gcagcggcag cagctgttag ggttttaaat    1080

aacaatgatc agattataaa gttatataaa gatcttgtta aattgaagcg tcatgcagga    1140

attaaaaaag ctatggaaga attggctgct caagacggag gttgtaatgg aggtggtgat    1200

aataagaaga agcgaggagc atctgaagac tctgatgcag gaggtgcttc taaaggaggg    1260

aaaggcaaag aaacaaaaga aacagagttt gatctgagta tgattgtcgg ccaagttaaa    1320

ctctatgctg acttatttac aactgaatca ttctcaatat atgctggtct tggtgcaggg    1380

ttagcttata cttctggaaa aatagatggt gtggacatta aagctaatac tggtatggtt    1440

gcatcaggag cacttggtgt agcaattaat gctgctgagg gtgtgtatgt ggacatagaa    1500

ggtagttata tgcattcatt cagtaaaata gaagagaagt attcaataaa tcctcttatg    1560

gcaagttttg gtgtacgcta taacttc                                        1587


<210> SEQ ID NO 12
<211> LENGTH: 1572
<212> TYPE: DNA
<213> ORGANISM: Orientia tsutsugamushi

<400> SEQUENCE: 12

atgaaaaaaa ttatgttaat tgctagtgca atgtctgcat tgtcattgcc gttttcagct      60

agtgcaatag aattgggtga ggaaggagga ttagagtgtg gtccttacgg taaagttgga     120

atcgttggag gaatgattac tggtgcagaa tctactcgct tggattcaac tgattctgag     180

ggaaaaaaac atttgtcatt aacaactgga ctgccatttg gtggtacatt agctgcgggt     240
```

-continued

```
atgacaattg caccaggatt tagagcagag ctaggtgtta tgtaccttag aaatataagc    300
gctgaggttg aagtaggtaa aggcaaggta gattctaaag gtgagataaa ggcagattct    360
ggaggtggga cagatactcc tatacgtaag cggtttaaac ttacaccacc tcagcctact    420
ataatgccta taagtatagc tgatcgtgat gtgggggttg atactgatat tcttgctcaa    480
gctgctgctg ggcaaccaca gcttactgtt gagcagcggg ctgcagatag gattgcttgg    540
ttgaagaatt atgctggtat tgactatatg gtcccagatc ctcagaatcc taatgctaga    600
gttataaatc ctgtattgtt aaatattact caagggccac ctaatgtaca gcctagacct    660
cggcaaaatc ttgacatact tgaccatggt cagtggagac atttggtagt tggtgttact    720
gcattgtcac atgctaataa acctagcgtt actcctgtca aagtattaag tgacaaaatt    780
actaagatat atagtgatat aaagccattt gctgatatag ctggtattga tgttcctgat    840
actggtttgc ctaatagtgc atctgtcgaa cagatacaga gtaaaatgca agaattaaac    900
gatgtattgg aagacctcag agattctttt gatgggtata tgggtaatgc ttttgctaat    960
cagatacagt tgaattttgt catgccgcag caagcacagc agcagcaggg gcaagggcag   1020
caacagcaag ctcaagctac agcgcaagaa gcagtagcag cagcagctgt taggctttta   1080
aatggcaatg atcagattgc gcagttatat aaagatcttg ttaaattgca gcgtcatgca   1140
ggagttaaga aagccatgga aaaattagct gcccaacaag aagaagatgc aaagaatcaa   1200
ggtgaaggtg actgtaagca gcaacaagga gcatctgaaa aatctaaaga aggaaaaggc   1260
aaagaaacag agtttgatct gagtatgatt gttggccaag ttaaactcta tgctgactta   1320
tttacaactg aatcattctc aatatatgct ggtgttggtg cagggttagc tcatacttat   1380
ggaaaaatag atgataagga tattaaaggg catacaggca tggttgcatc aggagcactt   1440
ggtgtagcaa ttaatgctgc tgagggtgta tatgtggact tagaaggtag ttatatgcac   1500
tcattcagta aaatagaaga gaagtattca ataaatcctc ttatggcaag tgtaggtgta   1560
cgctataact tc                                                        1572
```

TRUNCATED RECOMBINANT MAJOR OUTER MEMBRANE PROTEIN ANTIGEN (R56) OF *ORIENTIA TSUTSUGAMUSHI* STRAINS KARP, KATO AND GILLIAM AND ITS USE IN ANTIBODY BASED DETECTION ASSAYS AND VACCINES

CROSS-REFERENCE

This application is a divisional application filed under 37 CFR §1.53(b) of application Ser. No. 10/120,837 filed Apr. 12, 2002 (now U.S. Pat. No. 7,335,477), which is a Continuation-In-Part Application of application Ser. No. 09/218,425 filed Dec. 22, 1998 (now U.S. Pat. No. 6,482,415), which claims benefit to Provisional Application Ser. No. 60/482, 415, filed on Dec. 24, 1997 and U.S. Provisional Application Ser. No. 60/283,373 filed Apr. 13, 2001.

BACKGROUND OF THE INVENTION

Some of the most dreadful pandemics in the history of mankind result from the rapid spread of infectious diseases caused by virulent pathogenic organisms. These disease states are often accompanied by other opportunistic infections (viral, protozoal, bacterial or parasitic) and/or diseases due to the compromised immune system of infected patients.

There is new evidence that new epidemics are emerging throughout the industrialized, developing and transitional countries of the world.

Today, the rates of reported cases of diseases are increasing in exponential proportions and clinical treatments currently available represent only marginal improvements in the management of health care in this area. The rapid increase in the number of infectious diseases ranges from alarming to out of control. Unless improved treatments are found the future outlook for the state of the world's health is dismal. The scientific community throughout the world is mindful of the long-felt need for effective ways to (1) substantially reduce, eliminate, neutralize and/or kill virulent pathogenic organisms or agents, (2) inhibit the proliferation of rapidly replicating abnormal (infected or altered) cells caused by pathogenic organisms, or agents such as a virus, bacteria, fungus, venom, pollen, protozoal, and mixtures thereof and (3) identify effective vaccines, preventive (prophylactic) and therapeutic treatments for patients, including humans. In response to the need to alleviate suffering and provide comfort to human life, the scientific community is searching for effective means to inhibit the growth of rapidly proliferating abnormal mammalian cells caused by pathogenic organisms within the genus *Rickettsia,* such as *O. tsutsugamushi* alone and/or in combination with others.

Scrub typhus, also referred to as chigger-borne rickettsiosis, mite-borne typhus, Japanese river fever, tropical or rural typhus or *tsutsugamushi* disease is an acute, febrile disease caused by infection with *Orientia* (formerly *Rickettsia*) *tsutsugamushi*. It accounts for up to 23% of all febrile episodes in endemic areas of the Asia-Pacific region (5). The disease is characterized by a rise in body temperature, skin rash and severe headaches. This disease may affect the nervous system, with clinical manifestations such as delirium, stupor and muscle fibrillation. The death rate varies from 1 to 60% depending on the geographical regions. Scrub typhus, transmitted to mammals (including humans and cattle) through the bite of tiny trobiculid mites (arthropods) is particularly high is South-East Asia, Korea, Russia, Australia, China, Japan and India. The incidence of disease has increased in some countries during the past several years (6).

The causative organism is transmitted to human through the bite of tiny trobiculid mites. The organisms are found throughout the mite's body, but the highest number occurs in the salivary glands. When the mites feeds on mammals, including cattle, rodents or humans, the disease causing organisms are transmitted from the mite to the invertebrate host (subject). Scrub typhus infections are usually found in people engaged in activities that bring them inadvertently in contact with mite-infested habitats or any invertebrate host-carrier of these anthropods. These hosts may include domesticated, non-domesticated or farm animals, such as cattle or rodents. These hosts may be carrying mites which have not begun to feed on them. In this case, when the host is cattle, the live mites can be transferred from cattle to people. Individuals particularly susceptible include butchers, meatworkers, animal-farm workers and others engaged in outdoor activities. These persons could be infected by coming into contact with these mite-carrying animals. Additionally, rodents are capable of carrying and spreading infected mites to people in populated areas.

Only larval *Leptotrombidium* mites feed on vertebrate hosts. The larval mites acquire *O. tsutsugamushi* through their female parent. This type of pathogen reception is called "transovarial transmission."Once transmitted to the host, the organism incubates for about 10 to 12 days. From 5 to 8 days after infection, a dull read rash may appear all over the body, especially on the trunk. Mortality ranges from 1 to 60%. Death either occurs as a direct result of the disease, or from secondary effects, such as bacterial pneumonia, encephalitis, or circulatory failure. If death occurs, it is usually by the end of the second week of infection. Despite these tragic statistics, many people around the world do not understand or believe how deadly scrub typhus can be until it is too late. Unfortunately, too many people are unwittingly dancing with death.

FIELD OF THE INVENTION

This invention relates to detecting exposure to and identification of microorganism by the use of serodiagnostic assays, and more specifically to detecting exposure to and identification toward a truncated protein of at least one strain of *Orientia Tsutsugamushi* based on its strength in reactivity. Additionally, this invention related to the production of vaccines, passive prophylactic or therapeutic agents and detection or identification reagents. The products produced in accordance with this invention may be combined with other pharmaceutically-acceptable bioactive substances.

DESCRIPTION OF PRIOR ART

Scrub typhus is caused by *O. tsutsugamushi*, a gram negative bacterium. In contrast to other gram negative bacteria, *O. tsutsugamushi* has neither lipopoly-saccharide nor a peptidoglycan layer (1) and the ultrastructure of its cell wall differs significantly from those of its closest relatives, the typhus and spotted fever group species in the genus *Rickettsia* (33). The major surface protein antigen of *O. tsutsugamushi* is the variable 56 kDa protein which accounts for 10-15% of its total protein (16, 28). Most type-specific monoclonal antibodies to *Orientia* react with homologues of the 56 kDa protein (16, 24, 42). Sera from most patients with scrub typhus recognize this protein, suggesting that it is a good candidate for use as a diagnostic antigen (28).

Diagnosis of scrub typhus is generally based on the clinical presentation and the history of a patient. However, differentiating scrub typhus from other acute tropical febrile illnesses such as leptospirosis, murine typhus, malaria, dengue fever, and viral hemorrhagic fevers can be difficult because of the similarities in signs and symptoms. Highly sensitive polymerase chain reaction (PCR) methods have made it possible to detect *O. tsutsugamushi* at the onset of illness when antibody titers are not high enough to be detected (14, 19, 36). PCR amplification of the 56 kDa protein gene has been den demonstrated to be a reliable diagnostic method for scrub typhus (14, 28). Furthermore, different genotypes associated with different *Orientia* serotypes could be identified by analysis of variable regions of this gene without isolation of the organism (14, 17, 18, 25, 39). However, gene amplification requires sophisticated instrumentation and reagents generally not available in most rural medical facilities. Current serodiagnostic assays such as the indirect immunoperoxidase (IIP) test and the indirect immunofluorescent antibody (IFA) or microimmunofluorescent antibody (MIF) tests require the propagation of rickettsiae in infected yolk sacs of embryonated chicken eggs or antibiotic free cell cultures (4, 20, 30, 43).

At the present time the only commercially available dot-blot immunologic assay kids (Dip-S-Ticks) requires. tissue culture grown, Renografin density gradient purified, whole cell antigen (41). Only a few specialized laboratories have the ability to culture and purify *O. tsutsugamushi* since this requires biosafety level 3 (BL3) facilities and practices. The availability of recombinant rickettsial protein antigens which can be produced and purified in large amounts and have similar sensitivity and specificity to rickettsia-derived antigens would greatly reduce the cost, transport, and reproducibility problems presently associated with diagnostic tests which require the growth and purification of rickettsiae. Furthermore, large-scale growth and purification of the scrub typhus rickettsiae are prohibitively expensive.

Recently, a recombinant 56 kDa protein from Boryong strain fused with maltose binding protein was shown to be suitable for diagnosis of scrub typhus in a enzyme-linked immunosorbent assay (ELISA) and passive hemagglutination test (21, 22). Although this protein overcomes some of the above-described disadvantages, it still has certain inherent disadvantages as an assay reagent because it is a fusion protein.

SUMMARY OF THE INVENTION

Accordingly, an object of this invention is a recombinant DNA construct and expressed polypeptide possessing immunogenic regions for the Karp, Kato and Gilliam strains of *O. tsutsugamushi.*

Another object of the invention, as described herein, is a recombinant polypeptide encoding a portion of the 56 kDa protein of *O. tsutsugamushi* encoded by amino acids 80 to 456 for Karp strain SEQ ID NO.: 1, 81-453 for Kato strain SEQ ID No.: 4 and 81-448 for Gilliam strain SEQ ID NO.: 5.

A still further object of the invention is a recombinant truncated 56 kDa polypeptide which is re-folded to give a soluble moiety.

An additional object of this invention is the use of at least one recombinant polypeptide in antibody based assays for improved methods for the detection of *O. tsutsugamushi* exposure and/or identification of at least one of its Karp, Kato or Gilliam strains in research and in clinical samples.

Yet another object of the invention is the expression of truncated r56 polypeptides in different host backgrounds of bacterial strains for use in different vaccine formulations against scrub typhus infection.

These and other objects, features and advantages of the present invention are described in or are apparent from the following detailed description of preferred embodiments.

BRIEF DESCRIPTION OF THE DRAWINGS

The invention will be further described with reference to the drawings, in which like elements have been denoted throughout by like reference numerals. The representation in each of the figures is diagrammatic and no attempt is made to indicate actual scales or precise ratios. Proportional relationships are shown as approximations.

DETAILED DESCRIPTION

There is a critical need for rapid assays for the determination of exposure to *O. tsutsugamushi*, the causative agent of scrub typhus. Currently available assays require bacterial antigen which must be purified by extremely labor intensive methods after first propagating the organism in specialized laboratories (BSL-3). Further, there is currently no efficacious vaccine for scrub typhus.

Recombinantly produced protein antigens of *O. tsutsugamushi* and recognized by specific antibodies would greatly facilitate the practical use of anti-scrub typhus assays since the protein can be produced more economically. Additionally, recombinant polypeptides can be used in subunit vaccines.

In accordance with the practice of this invention, a recombinant, refolded non-fusion polypeptide expressed from a truncated r56 gene of the causative agent of scrub typhus, *Orientia tsutsugamushi* for the Karp, Kato and Gilliam strains has been produced. The invention is useful for detecting prior exposure to scrub typhus, screening for and/or identification of at least one infectious strain-similarity (i.e. a Karp-like, Kato-like, or Gilliam-like strain) based on its strength of reaction toward a truncated protein and as a component in vaccine formulations and production of immune globulins for passive prophylaxis and immunity in subjects.

The 56 kDa protein for *O. tsutsugamushi* is extremely abundant in the bacteria and is highly immunogenic. Although the use of recombinant 56 kDa protein from *O. tsutsugamushi* has been reported, it was produced as a fusion peptide which creates a number of inherent disadvantages, including reduced immunogenicity due to improper folding of the bacteria polypeptide. To overcome these problems a non-fusion, recombinant polypeptide from 56 kDa protein was produced using the following alternative procedures designated herein as PROCEDURES I and II to express and purify r56 from the Karp, Kato and/or Gilliam strains. Furthermore, as illustrated herein for the production of SEQ ID No. 1, in order to ensure proper folding of the polypeptide after translation, and therefore enhanced immune recognition, a truncated recombinant 56 kDa gene was created with the truncation created at specific points (Seq ID No. 1). The truncated 56 kDa gene is then expressed using efficient expression systems. This truncated, recombinant polypeptide is then use as antigen in antibody based assays and to induce an immune response against scrub typhus. The specification generally uses the Karp strain for illustrative purposes only, as the following examples apply to other strains of *O. tsutsugamushi*, including the Kato and Gilliam strains.

EXAMPLE 1

Cloning and Expression Of Recombinant 56 kDa Gene.

Figure 1:
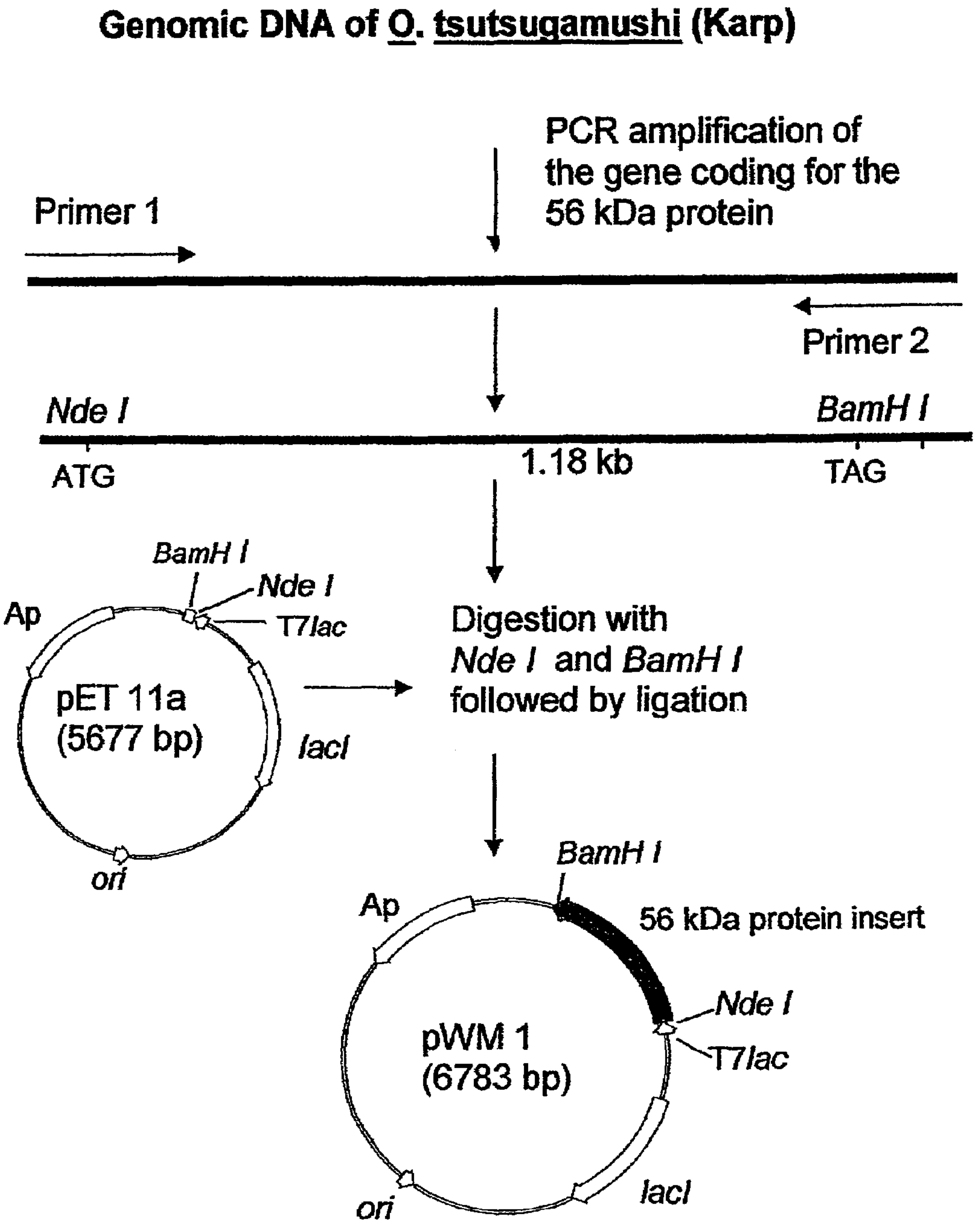
FIG. 1 shows the strategy for cloning and construction of pWM1 that expresses the truncated recombinant 56 kDa protein antigen from *O. tsutsugamushi* Karp strain.

As shown in FIG. 1, a primer pair (56F(226/261), 5'-TTGGCTGCACATATGACAATCGCTCCAGGAT TTAGA-3' (Seq. ID No. 2) and 56R (1409/1363), 5'-CTTTCTAGAAGTATAAGCTAACCCGGATCC AACACCAGCCTATATTGA-3'(Seq. ID No. 3) was designed using the nucleotide sequence of the open reading frame for the Karp 56 kDa protein (34). The respective restriction sites for Nde I and BamH I are underlined and the new initiation codon and reverse complement of the new stop codon are shown in bold and italic, respectively. The forward primer 56F (226/261) contained the methionine initiation codon, at residue 80, which is part of the Nde I recognition sequence. The reverse primer 56R (1409/1363) created an alteration of the tyrosine codon at residue 457 to a stop codon and contained a BamH I site. The coding sequence from amino acid 80 to 456 was amplified by polymerase chain reaction (PCR), using the above primers, from DNA isolated from plaque-purified *O. tsutsugamushi* Karp strain grown in irradiated L929 cells (18). The truncated 56 kDa gene was amplified in a mixture of 400 mM each of deoxynucleotide triphosphate, 1 mM of each primer, 1.5 U of Taq polymerase (Perkin-Elmer, CA) in 10 mM Tris-HCl buffer, pH 8.3, 1.5 mM $MgCl^2$, and 50 mM KCl. The PCR reaction was started with 15 sec at 80° C., 4 min at 94° C., and followed by 30 cycles of 94° C. for 1 min, 57° C. for 2 min and 72° C. for 2 min. The last cycle was extended for 7 min at 72° C. The amplified fragment (1.18 kb) was digested with Nde I (BioLab, MA) and BamH I (Life Technology, MD) and ligated with doubly digested expression vector. Any plasmid or viral expression system can be used as long as polypeptide is expressed. The preferred expression system is the plasmid system pET11a (Novagen, Wiss.) (FIG. 1) to yield the expression system pWM1. The *E. coli* strain HB101 was transformed with the ligation mixture and colonies screened for inserts with the right size and orientation.

Expressed r56 is constructed such that the N-terminal 79 residues or the C-terminal 77 residues of the intact 56 kDa protein, as deduced from the open reading frame of its encoding-gene, is not present. Both regions deleted were predicted to be relatively hydrophobic and be responsible for association with the rickettsial outer membrane. Truncation of these termini-facilitate the refolding of the expressed polypeptide and favors its solubility in aqueous solutions and simplification of handling.

Purification Of The 56 kDa Protein.

Figure 2:
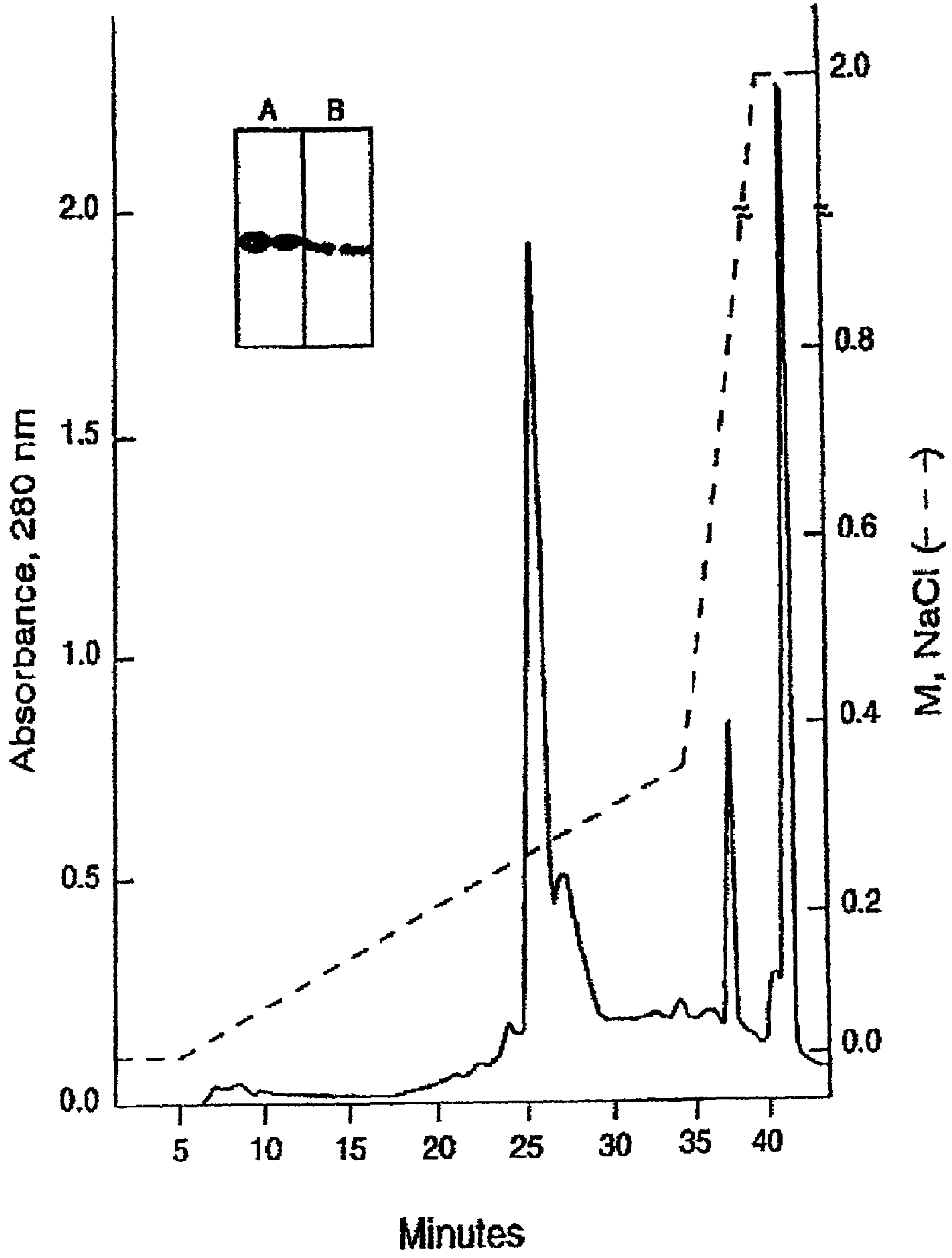
FIG. 2 shows the HPLC ion exchange profile for the purification of r56. The insert shows the Compassion blue staining (A) and Western blot analysis (B) of the two peak fractions at 25 (left lane) and 27 min (right lane) which contain most of the r56.

Plasmids carrying the insert of the truncated and amplified 56 kDa gene are transformed into the expression host *E. coli* BL21. The optimum time and IPTG concentration for r56 expression is determined. Recombinant *E. coli* expressing r56 are grown overnight at 37° C. with shaking. Cell pellets from 100 ml cultures are resuspended in 3 ml of buffer A (20 mM Tris-HCl, pH 8.0), containing 5 mM EDTA and 1 mM PMSF. Ultrasonic disruption of the cell is performed with cooling on ice. Disrupted cell extract is centrifuged at 8,000×g for 30 min. The pellets are vortexed to a homogeneous suspension with 2 M urea in buffer A, placed on a shaker at room temperature for an additional 10 min, centrifuged for 5 min at 14,000 rpm in an Eppendorf centrifuge (model 5415). The entire process is then repeated with 4 M urea in buffer A. Finally the pellets are dissolved in 8 M urea in buffer A and applied onto an HPLC ion exchange (DEAE) column (Waters, 0.75 cm×7.5 cm) for fractionation. Proteins are eluted with a linear gradient of buffer B and buffer C (6 M urea and 2 M NaCl in buffer A) from 0.0 to 0.4 M NaCl over 30 min at a flow rate of 0.5 ml/min. Fractions are collected, typically at one min per fraction. For a typical run, approximately 200 μl of extract obtained from a total of 10 ml culture is loaded onto the column (FIG. 2). The presence of r56 in fractions was detected by dot-blot immunoassay. Positive fractions with significant amounts of protein, presumably containing expressions of the truncated and amplified 56 kDa gene, are also analyzed by SDS-PAGE and Western blotting.

Testing for Polypeptide Expression by Dot-Blot Immunoassay.

Fractions collected from HPLC are screened for r56 polypeptide by dot-blot assay. A 2 μl sample of each eluted fraction is diluted into 200 μl of water and applied to a well of a 96-well dot blotter (Schleicher and Schuell). After drying under vacuum for 5 min, the nitrocellulose membrane is blocked with 5% nonfat milk for 30 min, then incubated with monoclonal antibody Kp56c specific for Karp 56 kDa protein antigen (23) for one hr, washed 4 times with phosphate buffer saline (PBS) 5 min each time, and incubated with peroxidase conjugated goat anti-mouse IgG (H+L) (Bio-Rad Laboratories) for 30 min. After washing with PBS 5 times for 5 min, substrate solution containing 5:5:1 ratio TMB peroxidase substrate, hydrogen peroxide solution, and TMB membrane enhancer (Kirkegaard and Perry Laboratories) is added onto the nitrocellulose membrane. The enzymatic reaction is stopped after 2 min by washing the membrane in distilled water. The above-described test can be incorporated onto any dot-blot, spot or dipstick type test structure. These structures are extensively described in the prior art.

Confirmation of Polypeptide Identity.

Confirmation of the identity of the polypeptide is confirmed by amino acid sequence analysis of SDS-PAGE purified, CNBr cleaved fragments of the peak fractions (7). The sequences are identical to that deduced from nucleotide.

Refolding of r56.

HPLC fractions, in 6 M urea, containing peak r56 polypeptide are pooled and sequentially dialyzed against 4 M urea and 2 M urea in buffer A and finally with buffer A only. The final dialysis is against buffer A with two initial-changes of buffer for 30 min each, and finally overnight at 4° C. r56 is properly folded since the polypeptide remains soluble in buffer A with no urea present.

Circular Dichroism (CD) Spectrum of r56.

The circular dichroism spectrum of refolded r56 was measured on a JASCO model 715 in Dr. Ettore Apella=s laboratory in NIH, Bethesda, Md. Data were analyzed by Dr. Latchezar I. Tsonev, Henry Jackson Foundation, Rockville, Md., at a protein concentration of 117 μg/ml in 20 mM TrisHCl, pH 8.0 and the calculated molecular weight of 40,903 dalton.

Figure 3:
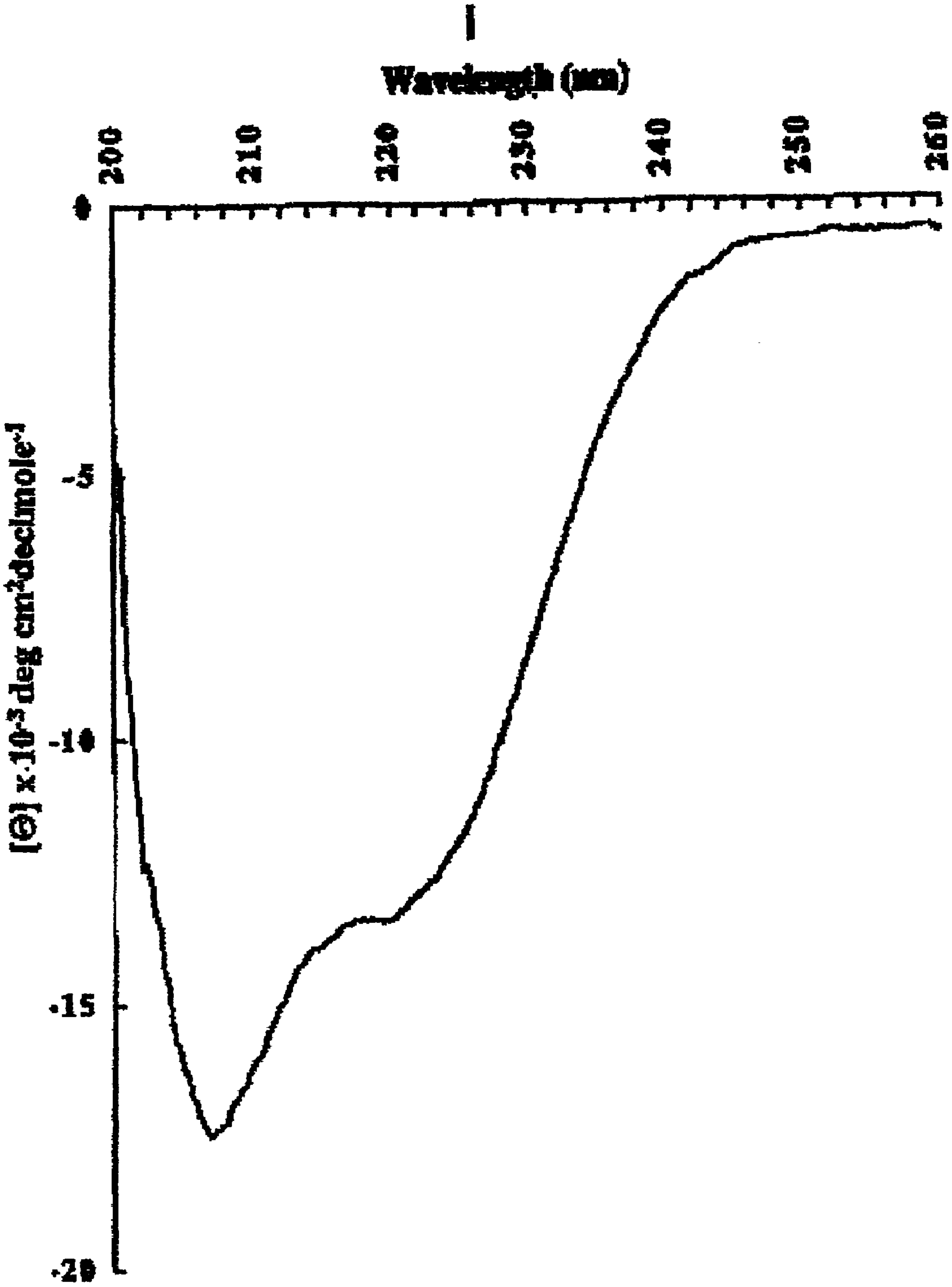
FIG. 3 shows the circular dichroism spectrum of refolded r56.

The CD spectrum of the refolded polypeptide shows that the secondary structure is approximately 38% α-helical, 13% β-sheet and 50% random coil (15) (FIG. 3). This experimental data is similar to that predicted by correctly folded, truncated 56 kDa protein, based on amino acid sequence from nucleic acid sequence (34).

EXAMPLE 2

Use of r56 Polypeptide in Antibody Based Identification Assays.

ELISA Assay Method

The microtiter plates are coated with antigens diluted in PBS overnight at 4° C. and blocked with 0.5% boiled casein for 1 hr, rinsed with PBS twice, 5 min each time. Patient sera are diluted 1:400 with 20 μg/ml of control protein extracts purified from *E. coli* BL21 using a procedure identical to that used for purifying r56 (fractions 21-32 pooled from gradients equivalent to FIG. 2), pre-absorbed for about 1 hr at room temperature, and then added to the ELISA plates. The plates are incubated for 1 hr at room temperature, washed four times with 0.1% Triton X-100 in PBS. Peroxidase conjugated mouse anti-human IgG (Fc specific) (Accurate) diluted 1:8000 and goat anti human IgM (μ chain specific) (Kirkegaard & Perry) are then added. After 1 hr incubation at room temperature, the plates are washed four times with 0.1% Triton X-100 in PBS and the last wash is with PBS only before the addition of substrate ABTS (Kirkegaard & Perry). The ODs at 405 nm are read after 15 min incubation at room temperature. Rabbit sera were diluted 1:250 with PBS only. All procedures are the same as for detection of human antibodies except that rabbit sera is not preabsorbed with protein preparations from BL21 and peroxidase conjugated goat anti-rabbit IgG (Kirkegaard & Perry) diluted 1:2,000 is used.

Figure 4:
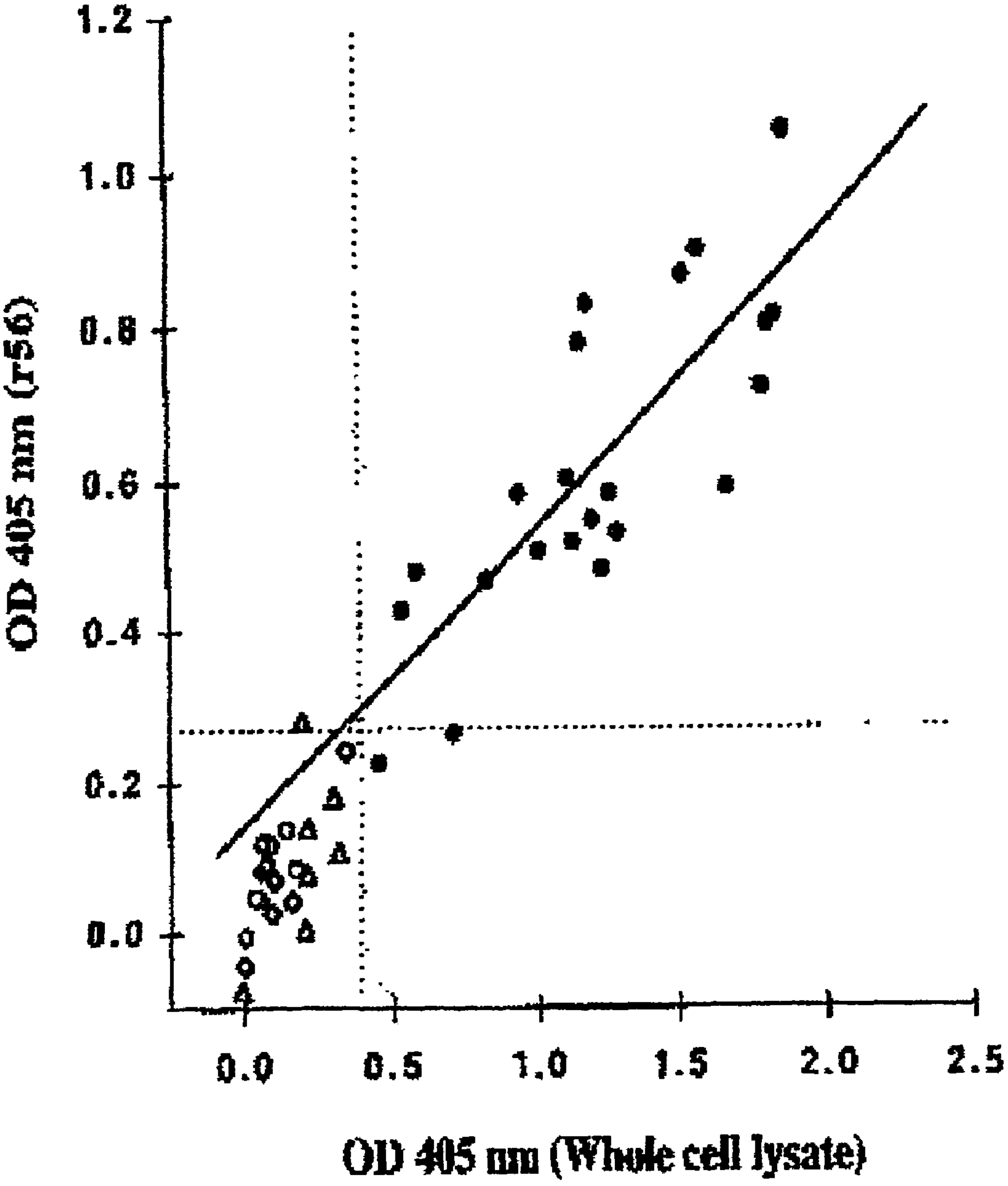
FIG. 4 shows a comparison of ELISA IgG reactivity of r56 and *O. tsutsugamushi* Karp strain whole cell lysate with rabbit antisera (see Table 1).

The recombinant r56 polypeptide contains only a portion of the 56 kDa protein, the major antigen that is used to differentiate antigenic types of *Orientia*. In addition rickettsial whole cell lysate contains numerous other protein antigens besides intact 56 kDa antigen. A comparison of ELISA IgG reactivity of r56 and *O. tsutsugamushi* Karp strain whole cell lysate with rabbit antisera is shown (FIG. 4). The dotted lines represent the mean+2 standard deviations of reactivity of the normal rabbit sera. The solid line is the linear regression of the data for the 22 anti-*Orientia* rabbit sera tested (r=0.81). Eight control normal rabbit sera (open diamonds); five antisera against non-rickettsial antigens (open triangles): eight antisera to Rickettsiales other than *Orientia* (open squares); and 22 antisera to eight antigen prototypes of *O. tsutsugamushi* (solid circles) are compared. Positive breakpoints (mean+2 SD) for reactivity of both r56 and whole cell *Orientia* lysate (WCEX) and standard ELISA using eight normal rabbit (ODs of 0.27 and 0.38), respectively, are established. (FIG. 4, Table 1). None of the eight rabbits immunized with other species of Rickettsiales or the five antisera prepared against either L-cell, yolk sac, or *E. coli* exhibit reactivity higher than the cutoff for WCEX while one rabbit antiserum against primary chick embryo reacted barely above the breakpoint with r56 (OD of 0.28) (FIG. 4, Table 1). On the other hand 20 of 22 rabbit antisera against the eight *Orientia* antigenic prototypes react slightly above the breakpoint with r56 and all sera exhibit positive ELISA with WCex (FIG. 4, Table 1). Although the r56 antigen exhibits lower ELISA reactivity at the amount employed than that obtained with WCEX, the *Orientia* rabbit antisera exhibit a very good correlation of ELISA reactions to the two antigens (r=0.8, n=22). One Kato antiserum and one TA686 antiserum which exhibit relatively low positive ELISA reactivity with WCex does not react, significantly, with r56 antigen (Table 1). Consequently, the ELISA with folded r56 gives equivalent results as the standard ELISA in the detection of *Orientia*-specific antibodies by ELISA (specificity-92.3%, sensitivity-90.9%, accuracy-91.4%) with WCEx ELISA as the reference assay) even though r56 is only a truncated portion of one of the complex antigens found in WCex.

TABLE 1

Comparison of ELISA reactivity of purified Karp whole cell lysate and folded r56 with rabbit antisera.
Antisera against ELISA ODs (405 nm) or whole cell lysate
Different antigens (corresponding r56 result)

| | |
|---|---|
| | *O. tsutsugamushi* strain |
| Karp | 0.94 (0.58), 1.87 (1.04), 1.81 (0.80), 1.83 (0.81) |
| Kato | 0.46 (0.22), 1.02 (0.50), 1.16 (0.77), 1.27 (0.58) |
| Gilliam | 0.54 (0.42), 1.20 (0.54) |
| TH1817 | 1.67 (0.59), 1.12 (0.60), 1.29 (0.53), 0.83 (0.47) |
| TA678 | 0.59 (0.48) |
| TA686 | 0.71 (0.26), 1.52 (0.86) |
| TA716 | 1.24 (0.48), 1.14 (0.51) |
| TA763 | 1.79 (0.72), 1.57 (0.89), 1.18 (0.82) |
| | Other Rickettsiales |
| *R. prowazekii* | 0.08 (0.12) |
| *R. typhi* | 0.18 (0.08) |
| *R. rickettsii* | 0.06 (0.04), 0.15 (0.14) |
| *R. conorii* | 0.10 (0.11), 0.07 (0.11) |
| *E. sennetsu* | 0.01 (0.05) |
| *E. risticii* | 0.01 (−0.01) |
| | Non rickettsial antigens |
| Yolk sac | 0.22 (0.08) |
| L929-cell | 0.01 (−0.08) |
| Primary chick embryo | 0.20 (0.28) |
| RAW 264.7 cells | 0.22 (0.14) |
| *E. coli* HB101 | 0.32 (0.11) |
| No antigen control (n = 8) | 0.135 + 0.123 (0.093 + 0.088) |

OD values listed are the difference between data with antigen and without antigen.

Comparison of r56 ELISA with IIP Test with Human Sera.

Figure 5:
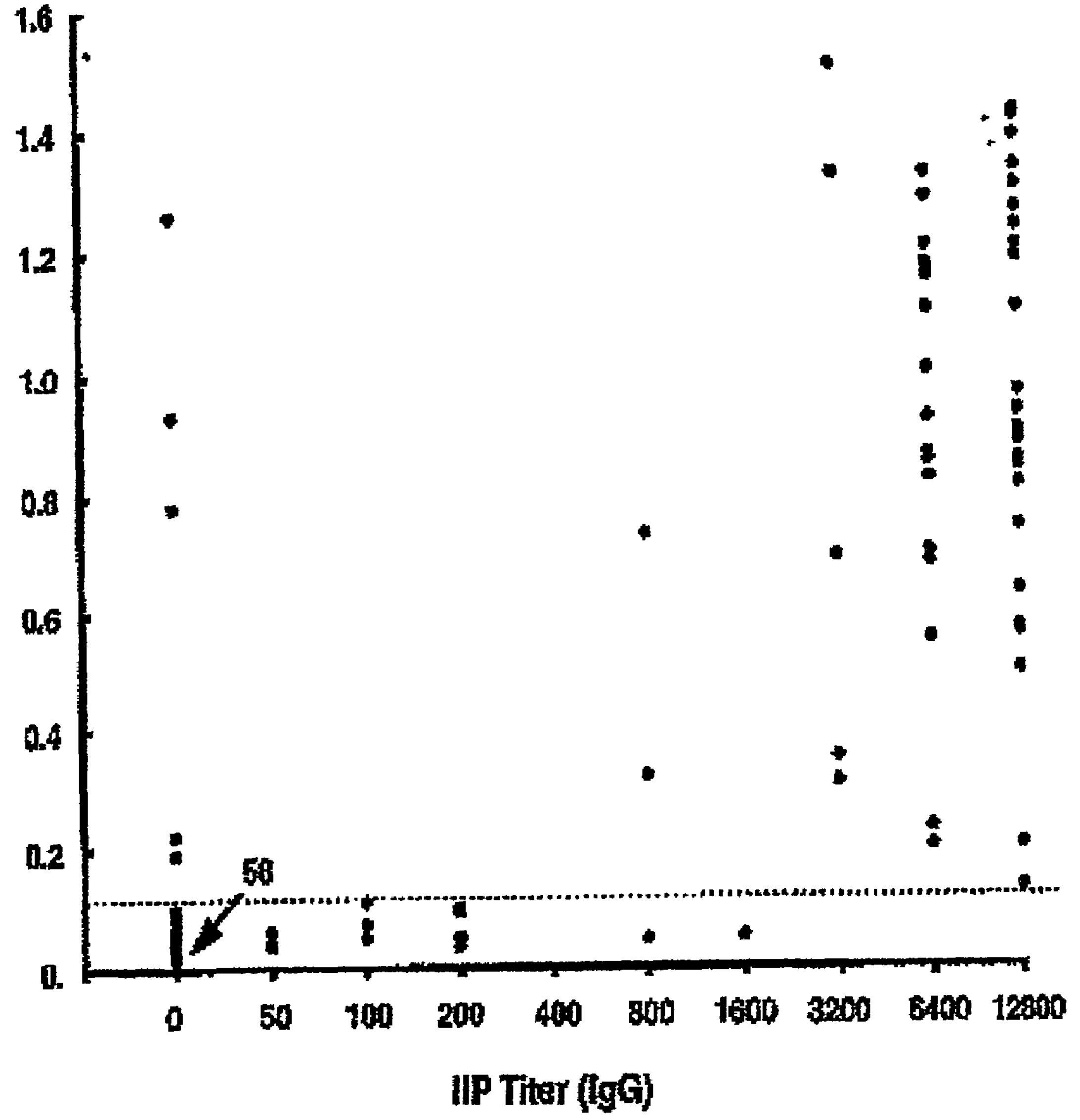
FIG. 5 shows a scattergram of IgG ELISA reactivity of 128 Thai patient sera obtained with folded r56 and the corresponding IIP test IgG titers.
Figure 6:
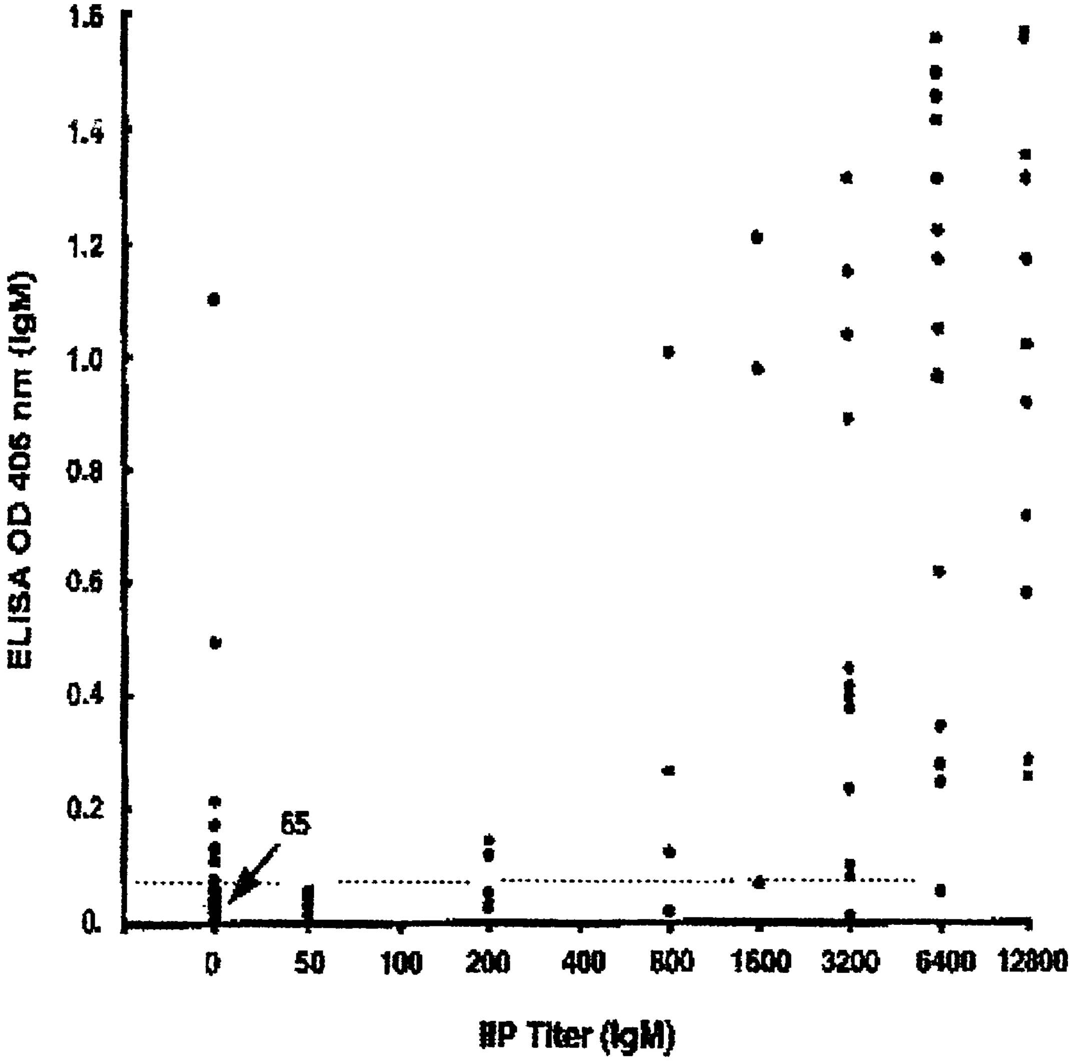
FIG. 6 shows a scattergram of IgM ELISA reactivity of 128 Thai patient sera obtained with folded r56 and the corresponding IIP test IgM titers.

Seventy-four sera from healthy Thai soldiers were used to establish an ELISA break point for positive reactions (mean+2 SD) with r56 as antigen. These are 0.05+0.06=0.11 OD for IgG, and 0.032+0.032=0.064 OD for IgM at 1:400 serum dilution. The r56 ELISA ODs of 128 sera from patients suspected of scrub typhus from Korat, Thailand were compared with the IgG and IgM titers determined by an IIP method using a mixture of intact Karp, Kato, and Gilliam prototypes of *Orientia*. The IIP method used was described previously (20, 38) (FIGS. 5 and 6). Using IIP titers as the gold standard, the sensitivity, specificity, and accuracy values of ELISA results with the 128 test sera are calculated using different positive breakpoints for the IIP test (Table 2).

TABLE 2

Comparison of efficiency of r56 ELISA with the indirect immunoperoxidase assay (IIP) for 128 Thai patient sera.

| | | | Elisa | | |
|---|---|---|---|---|---|
| Titer | IG | No. pos. sera by IIP | % Sensitivity | % Specificity | % Accuracy |
| 1:50 | IgG | 68 | 82% | 92% | 87% |
| | IgM | 56 | 91% | 92% | 91% |
| 1:200 | IgG | 61 | 92% | 93% | 92% |
| | IgM | 52 | 98% | 92% | 95% |
| 1:400 | IgG | 57 | 90% | 93% | 95% |
| | IgM | 47 | 100% | 93% | 93% |

Figure 7:
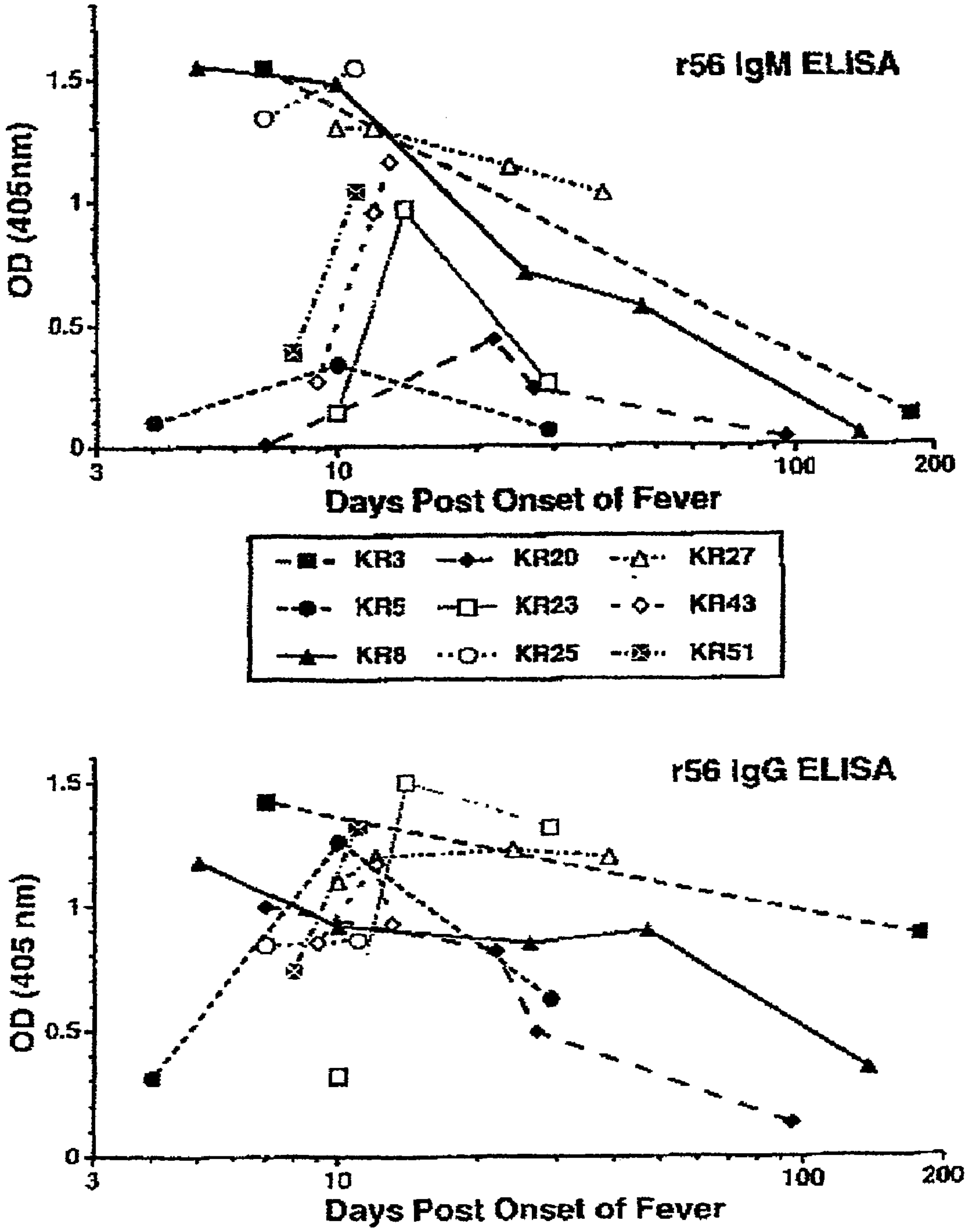
FIG. 7 shows the time course if IgM and IgG reactivity of confirmed cases of scrub typhus by ELISA with folded r56 as antigen.

Sera from 13 isolate and PCR-confirmed cases of scrub typhus were analyzed to characterize the kinetics and magnitude of the IgM and IgG immune responses as measured by IIP test titers and by r56 ELISA ODs. Representative data are shown in FIG. 7 and Table 3. Four sera from 4 different cases were available from the first week after onset of fever (days 4-7). All are positive by IIP for both IgM and IgG with titers between 3200 and 12,800 for all cases. In contrast, by ELISA, KR5 (day 4, table 3) has very low IgM and IgG ODs and KR20 is negative for Igm even at day 7 while the other two sera (KR8, KR25) are more reactive by IgM assay than IgG. Sixteen sera from 12 cases were collected 8-14 days post inset of fever. By IIP both IgM and IgG titers are again high and within one two-fold dilution for all of these sera except the day 10 serum from KR23 which also has the lowest IgM and IgG ELISA OD's (Table 3, FIG. 7). Except for three other sera from days 8-10 (KR5, KR43, KR51) which also had low IgM ODs, most sera has similar IgG and IgM ELISA reactions. Five sera from four cases were obtained in weeks 3-4 after infection. Two of the cases (KR8, KR20) exhibit a decrease in IgM ODs by ELISA at this time point which are not apparent by IIP assay while the other reactions all remain strong. In weeks 5-6 after infection two of 5 sera from different patients decline in IIP IgM titers (but not IgG titers) while three sera decline significantly in ELISA IgM and one by ELISA IgG. In striking contrast, KR 27 maintain high levels of specific antibody as measured by all assays from 10 to 39 days (Table 3). With all six sera collected from six different cases 95-202 days post onset of illness, IgM IIP titers and both IgM and IgG ELISA ODs drop significantly; in contrast, only one of the sera exhibit a decline in IgG IIP titers (FIG. 7).

TABLE 3

Comparison of IIP test titers with EILSA r56 OD's obtained with human sera from confirmed cases of scrub typhus.

| | Days post | IIP Test Titer | | r56 ELISA(OD) | |
|---|---|---|---|---|---|
| Patient | Onset of fever | IgM | IgG | IgM | IgG |
| KR5 | 4 | 3,200 | 3,200 | 0.10 | 0.31 |
| KR5 | 10 | 6,400 | 12,800 | 0.34 | 1.26 |
| KR5 | 29 | 1,600 | 12,800 | 0.07 | 0.63 |
| KR8 | 5 | 12,800 | 12,800 | 1.55 | 1.18 |
| KR8 | 10 | 6,400 | 6,400 | 1.48 | 0.92 |
| KR8 | 26 | 12,800 | 12,800 | 0.71 | 0.85 |
| KR8 | 47 | 12,800 | 12,800 | 0.57 | 0.90 |
| KR8 | 137 | 50 | 3,200 | 0.05 | 0.35 |
| KR10 | 10 | 12,800 | 6,400 | 1.30 | 1.15 |
| KR10 | 201 | 200 | 6,400 | 0.053 | 0.20 |
| KR20 | 7 | 3,200 | 6,400 | 0.01 | 1.00 |
| KR20 | 22 | 3,200 | 6,400 | 0.44 | 0.82 |
| KR20 | 27 | 6,400 | 12,800 | 0.24 | 0.50 |
| KR20 | 95 | 200 | 6,400 | 0.03 | 0.13 |

TABLE 3-continued

Comparison of IIP test titers with EILSA r56 OD's obtained with human sera from confirmed cases of scrub typhus.

| | Days post | IIP Test Titer | | r56 ELISA(OD) | |
|---|---|---|---|---|---|
| Patient | Onset of fever | IgM | IgG | IgM | IgG |
| KR23 | 10 | 200 | 800 | 0.14 | 0.32 |
| KR23 | 14 | 1,600 | 3,200 | 0.97 | 1.50 |
| KR23 | 29 | 800 | 3,200 | 0.26 | 1.32 |
| KR25 | 7 | 12,800 | 12,800 | 1.34 | 0.84 |
| KR25 | 11 | 6,400 | 6,400 | 1.54 | 0.86 |
| KR27 | 10 | 3,200 | 6,400 | 1.30 | 1.10 |
| KR27 | 12 | 6,400 | 12,800 | 1.30 | 1.20 |
| KR27 | 24 | 3,200 | 12,800 | 1.14 | 1.23 |
| KR27 | 39 | 3,200 | 12,800 | 1.03 | 1.20 |
| KR43 | 9 | 6,400 | 6,400 | 0.27 | 0.85 |
| KR43 | 12 | 6,400 | 6,400 | 0.96 | 1.17 |
| KR43 | 13 | 12,800 | 12,800 | 1.16 | 0.93 |
| KR51 | 8 | 3,200 | 12,800 | 0.39 | 0.74 |
| KR51 | 11 | 6,400 | 6,400 | 1.04 | 1.32 |

The excellent sensitivity and specificity of the r56 ELISA in comparison with those of the IIP assay suggest that one protein antigen, i.e. truncated r56, is sufficient for detecting anti-*Orientia* antibody in sera from patients with scrub typhus. Use of a single moiety in recombinant form improves efficiency of the assay and will reduce cost per assay, significantly.

EXAMPLE 4

Induction of Protective Immune Response.

Because of the significant antibody response exhibited after exposure with *O. tsutsugamushi* in rabbits and human, and the excellent recognition pattern of r56 polypeptide compared to whole cell extracts, the r56 polypeptide is a good candidate vaccine component.

Two strains of either relatively outbred mice (CD1) or an inbred strain (C3H) were immunized, with adjuvant with the r56 polypeptide. At various times after administration of the polypeptide the animals were challenged with live *O. tsutsugamushi.*

The protective efficacy of administration of r56 polypeptide is shown in table 4.

TABLE 4

Protection of Mice by Immunization with r56

| Experiment | Strain of mice | Dose/Mouse (adjuvant) | Challenge date post immunization | % Protection |
|---|---|---|---|---|
| I | C3H | 25 μg (incomp. Freunds) | 3 weeks | 100% |
| II | CD1 | 25 μg (Titer Max) | 4 months | 60% |
| III | CD1 | 2 μg (Titer Max) | 4 weeks | 60% |

Karp, Kato and Gilliam Strains

The variable 56 kDa major outer membrane protein of *Orientia tsutsugamushi* is the immunodominant antigen in human scrub typhus infections. The gene encoding this protein from Gilliam strain and Kato strain was cloned into the expression vector pET24a. The recombinant protein (r56) was expressed as a truncated non-fusion protein (amino acid 81 to amino acid 488 of the open reading frame for Gilliam and amino acid 81 to amino acid 453 of the open reading frame for Kato strain). Both protein formed an inclusion body when expressed in *Escherichia coli* BL21. The refolded r56 (Gilliam) and r56 (Kato) were mixed at an equal ratio and used as the antigen in an ELISA. A panel of patient sera exhibiting a wide range of reactivity was employed to compare the reactivity of mixed recombinant r56 antigens with mixed whole cell antigens. The ELISA results correlated well to those obtained using whole cell lysate from the corresponding strains as the coating antigen in the ELISA. These results strongly support that the mixture of the recombinant proteins has the coating antigen in the ELISA. These results strongly support that the mixture of the recombinant proteins has the potential to be used as a diagnostic reagent, exhibiting broad sensitivity and high specificity for scrub typhus infection and in production of immune globulins., vaccines, and therapeutic agents. The recombinant r56 (Gilliam) and r56 (Kato) have the potential to replace the density gradient-purified, *rickettsia*-derived, whole cell antigen currently used in the commercial dipstick assay available in the USA.

The molecular cloning, expression, purification, and refolding of the truncated non-fusion 56 kDa protein from Gilliam strain, r56 (Gilliam), and from Kato strain, r56 (Kato) will now be described. The refolded r56 (Gilliam) reacted strongly with monoclonal antibody (mAb) RK-G3C51 but did not react with mAb E+95. The r56 (Kato) reacted with E+95, but not with RK-G3C51. The strain variations of *Orientia* are well documented. In order to develop a diagnostic reagent that will detect most cases of scrub typhus infection, different serotype antigens need to be included in the antigen cocktail employed. A mixture of three purified recombinant r56 (Karp, Gilliam and Kato) was evaluated for its reactivity with 20 patient sera which exhibited wide range of reactivity with whole cell lysate cocktail of strains Karp, Gilliam, and Kato in a standard ELISA for diagnosis of scrub typhus. The ELISA results of using mixture of r56 correlated well to those obtained using the mixture of corresponding strains of whole cell lysate. These results strongly suggest that the recombinant proteins have the protential to be used as diagnostic reagents, exhibiting broad sensitivity and high specificity for scrub typhus infection.

Bacterial strains and vectors. *Eschericia coli* HB101 was used for cloning and *E. coli* BL21 (DE3) was used for over-expression of proteins under the control of phage T7lac promoter (26). The plasmid vector used was pET-24a (Novagen, Madison, Wiss.). Plaque-purified *O. tsutsugamushi* Gilliam and Kato strains were grown in irradiated L929 cells was used for preparation of the genomic DNA (11).

Cloning of the gene for the r56 (Gilliam) into the expression vector pET24A.

```
A primer pair 56FGm (784/819),
                                        (SEQ ID No. 6)
5' TTA GCT GCG C↓ATA TG ACA ATT GCA CCA GGA TTT

AGA 3'
and

r56RGm (1929/1894)
                                        (SEQ ID No. 7)
5' ATG AGC TAA CCC G↓GA TCC AAC ACC AGC CTA TAT

TGA 3'
```

was designed using the nucleotide sequence of the open reading frame for the Gilliam 56 kDa protein (27). The respective restriction sites for Nde and BamH I are underlined and bold. The forward primer 56FGm (784/819) contained the methionine initiation codon, at residue 81, which is part of the Nde I recognition sequence. The reverse primer 56RGm (11929/1894), mutated the tyrosine codon at residue 448 to a stop codon and contained a BamH I site. The coding sequence from amino acid 81 to 448 was amplified by PCR from DNA isolated from *O. tsutsugamushi* Gilliam strain.

Cloning of the gene for the r56 (Kato) into the expression vector pET24a.

```
A primer pair 56FKt (785/820),
                                        (SEQ ID No.8)
5' TTA GCT GCA C↓A TA TG ACA ATC GCG CCA GGA TTT
AGA 3'
and

r56RKt (1945/1910),
                                        (SEQ ID No. 9)
5' ATA AGC TAA CCC G↓GA TCC AAG ACC AGC CTA TAT
TGA 3'
```

was designed using the nucleotide sequence of the open reading frame for the Kato 56 kDa protein (31). The respective restriction sites for Nde I and BamH I are underlined and bold. The forward primer 56FGm (784/819) contained the methionine initiation codon, at residue 81, which is part of the Nde I recognition sequence. The reverse primer 56RGm (11929/1894), mutated the tyrosine codon at residue 448 to a stop codon and contained a BamH I site. The coding sequence from amino acid 81 to 448 was amplified by PCR from DNA isolated from *O. tsutsugamushi* Gilliam strain.

The two truncated 56 kDa genes were amplified in a mixture of 400 mM each for deoxynucleotide triphosphate, 1 mM of each primer, 1.5 U of Taq polymerase (Perkin-Elmer-Cetus, Norwalk, Conn.) in 10 mM Tris-HCl buffer, pH 8.3, 1.5 mM MgCl2, and 50 mM KCl. The PCR reaction was started with 15 sec at. 80° C., 4 min at 94° C., and followed by 30 cycles of 94° C. for 1 min, 57° C. for 2 min and 72° C. for 2 min. The last cycle was extended for 7 min at 72° C. The amplified fragments was digested with Nde I (New England BioLabs, Beverly, Mass.) and BamH I (GIBCO-BRL Life Technology, Gaithersburg, Md.) and ligated with doubly digested expression vector pET24a. *E. coli* HB101 was transformed with the ligation mixture and colonies screened for inserts with the right size and orientation.

Procedure I

Expression and purification of the r56 (Gilliam) and r56 (Kato). Plasmids carrying the insert were transformed into the expression host *E. Coli* BL21. -The optimum time and isopropyl- -D-thiogalactopyranoside (IPTG) concentration for inducing r56 expression was determined. Recombinant *E. coli* expressing r56 (Gilliam) were propagated overnight in 2X TY (16 g bacto-tryptone, 10 g bacto-yeast extract, and 5 g NaCl per liter of distilled water, pH 7.0) at 37° C. with shaking. Cell pellets from 100 ml cultures were resuspended in 3 ml of buffer A (20 mM Tris-HCl, pH 8.0), containing 5 mM EDTA. Ultrasonic disruption of the cell was performed using setting 3 on a Sonicator Ultrasonic Liquid Processor Model XL2020 with standard tapered microtip (Heat Systems, Inc., Farmingdale, N.Y.), six times for 20 sec with cooling on ice for 1 min between each sonication. Disrupted cell extract was centrifuged at 8,000×g for 30 min. The pellets were vortexed to a homogeneous suspension with 2 m urea in buffer A, placed on a shaker at room temperature for an additional 10 min, centrifuged for 5 min at 14,000 rpm in an Eppendorf centrifuge (model 5415). The entire process was then repeated with 2% sodium deoxycholate in buffer A. Finally the pellets were dissolved in 8 M urea in buffer A. The supernant was applied onto an high pressure liquid chromatography (HPLC) ion exchange (DEAE 5PW) column (Waters Associates, Milford, Mass.) (0.75 cm×7.5 cm) for fractionation. Proteins were eluted with a linear gradient of buffer B (6 M urea in buffer A) and buffer C (6 M urea and 2M NaCl in buffer A) from 0.0 to 0.4 M NaCl over 30 min at a flow rate of 0.5 ml/min. Fractions were collected at one min per fraction. The presence of r56 in fractions was detected by dot blot immunoassay. Positive fractions with significant amounts of protein were analyzed by SDS-PAGE and Western blotting.

Dot Blot immunoassay. A 2 μl sample of each eluted fraction was diluted into 200 μl of water and applied to a well of 96-well dot blotter (Schleicher and Schuell, Keene, N.H.). After drying under vacuum for 5 min, the nitrocellulose membrane was blocked with 5% nonfat milk for 30 min, then incubated with antibody specific for Gilliam or Kato 56 kDa protein antigen for 1 hr, washed 4 times with phosphate buffer saline (PBS) 5 min each time, and incubated with peroxidase conjugated goat anti-mouse IgG (H+L) (Bio-Rad Laboratories, Richmond, Calif.) for 30 min. After washing with PBS 5 times for 5 min, substrate solution containing 5:5:1 ratio of TMB (tetramethylbenzidine) peroxidase substrate, hydrogen peroxide solution, and TMB membrane enhancer (Kirkegaard and Perry Laboratories, Gaithersburg, Md.) was added onto the nitrocellulose membrane. The enzymatic reaction was stopped after 2 min by washing the membrane in distilled water.

SDS-PAGE and Western Blot analysis. Sodium dodecyl sulfate-polyacrylamide gel electrophoresis (SDS-PAGE) analysis was performed with the mini-protein II Dual Slab Cell System (8.2 cm×7.2 cm×0.75 cm, Bio-Rad). The stacking gel and separation gel contained 4% and 10% acryl amide (acrylamide:bisacrylamide ration was 30:1), respectively. Electrophoresis was carried out as constant voltage of 125 V for 75 min. The gels were either stained with Compassion Blue R or electroblotted onto nitrocellulose membrane. Immunodetection of the Western blot was the same as described for the dot blot immunoassay.

Refolding of r56. Refolding of r56 (Gilliam) and r56 (Kato) in 6 M urea in buffer A were achieved by sequential dialysis with h4 M urea and 2 M urea in buffer A and finally with buffer A only. The peak fractions from the DEAE column were combined and dialyzed against 8 volumes of 4 M urea in buffer A for 30 min at room temperature followed with one change of the dialysis solution and dialyzed for an additional 30 min. The same procedure was repeated with 2 M urea in buffer A. The final dialysis was against buffer A with two initial changes of buffer for 30 min each, and finally overnight at 4° C.

Human sera. Patient sera were collected from Pescadore Islands in 1976 (2).

ELISA. 96 well microtiter plates were coated overnight at 4° C. with antigens diluted in PBS and blocked with 0.5% boiled casein for 1 hr, rinsed with PBS twice, 5 min each time. Linbro U plates (Cat. No. U 76-311-05, ICN, Costa Mesa, Calif.) were used for assays with rabbit sera while Microtest III tissue culture plates (Falcon #3072) were employed with human sera. Patient sera were diluted 1:100 in PBS. The plates were incubated for 1 hr at room temperature, washed four times with 0.1% Triton X-100 in PBS. Peroxidase conjugated mouse anti-human IgG (Fc specific) (Accurate Chemical and Scientific Corp, Westbury, N.Y.) diluted 1:2000. After 1 hr incubation at room temperature, the plates were washed four times with 0.1% Triton X-100 in PBS and the last wash was with PBS only before the addition of substrate ABTS (Kirkegaard & Perry). Optical densities (ODs) at 405 nm were measured at 10 min and 15 min at room temperature.

Table 5 lists the ELISA data of 20 patient sera. The ELISA results using the mixture of three recombinant r56 polypeptides correlated well to those obtained using whole cell lysate from the corresponding strains as the coating antigen. A basic problem in the design of diagnostic tests for *Orientia* is that numerous serotypes exist. Eight prototypes (Gilliam, Karp, Kato, TA686, TA716, TA678, TA763, TA1817) have been widely used as reference strains for MIF serotyping of isolates collected throughout the areas endemic for *Orientia* (7, 24). In recent years several additional serotypes from Japan and Korea have been recognized (5, 22, 33). We have recently characterized more than 200 *Orientia* isolates by restriction fragment length polymorphism (RFLP) analysis of four different antigen gene homologues following their amplification by polymerase chain reaction (6, 11). 45 RFLP variant types were identified. The dominant human immune response is against the variable 56 kDa outer membrane protein which is the major antigen distinguished in serotyping. Some of the antigenic serotypes found in Japan and Taiwan have recently been further subdivided by RFLP analysis of their 56 kDa genes (10, 18, 29). Both specific and cross-reactive domains exist in different homologues of this protein. DNA sequence analysis of 56 kDa genes from various serotypes has revealed that the sequences may be divided into four conserved and four variable domains (19). These conserved domains of 56 kDa protein may account for the cross-reactivity of antisera against diverse serotypes while the variable domains are very likely responsible for some of the serotype specification observed in *Orientia*. The r56 recombinant proteins lack most of the conserved regions of the 56 kDa protein at both the N- and C-terminus. The conserved regions between the first and the second variable domain and between the second and the third variable domain are relatively short. Consequently, the broad reactivity of r56 may be due to the conserved region located between the third and the fourth variable domain which is about 160 residue long. The four variable domains are responsible for the strain specificity in serological tests. The *O. tsutsugamushi* strains Karp, Gilliam, and Kato have been shown to be antigenically distinct. They were isolated from different geographic areas (Karp from New Guinea, Gilliam from Burma, Kato from Japan). Recently a rapid flow assay for diagnosis of scrub typhus using r56 (Karp) (36, 27) was developed. To improve upon the broad reactivity of this RFA, the r56 antigens were produced from strains Gilliam and Kato to be included in the RFA for future evaluation at clinical sites.

In summary, the 56 kDa major variable outer membrane protein antigen of *O. tsutsugamushi* is the immunodominant antigen in human infections. Further, the strain variations of *Orientia* are well documented. In order to develop a diagnostic reagent that will detect most cases of scrub typhus infection, the preferred embodiment of the invention includes the r56 Karp antigen alone, when prepared by PROCEDURE II or in combination with or b. most preferably, a combination of different serotype antigens in the antigen cocktail employed.

The gene encoding this protein from the Karp strain (amino acid 80-456, designated as r56) was cloned, expressed, and purified in accordance with PROCEDURE I.

In following PROCEDURE I relative to the Kato and Gilliam strains, the 56 kDa protein from the Kato strain and the Gilliam strain were expressed with slight modifications to the procedure (PROCEDURE I) that was used to express and purify r56 from the Karp strain. This modification is attributable to the use of different primer in the production of each of the r56 Karp (SEQ ID NO. 1), r56 Kato (SEQ ID NO. 4), and r56 Gilliam (SEQ ID NO. 5) polypeptides. The r56 Gilliam and r56 Kato are truncated at both the N and C-termini, and exhibited the expected size by SGS-PAGE (amino acids 81-448 for r56 Gilliam, total of 368 amino acids; amino acids 81-453 for r56 Kato, total of 373 amino acid). The r56 Gilliam did not react with monoclonal antibody E+95 but reacted strongly with RK-G3C51. The r56 Kato reacted with E+95, but not with RK-G3C51. These three r56 antigens were mixed at an equal ratio and used as the antigen in an ELISA. A panel of patient sera exhibiting a wide range of reactivity was employed to compare the reactivity of mixed recombinant r56 antigens with mixed whole cell antigens. The ELISA results correlated well to those obtained using whole cell lysate from the corresponding strains as the coating antigen in the ELISA. These results provide strong scientific evidence which supports that the mixture of the recombinant proteins has the potential to be sued as a diagnostic reagent, exhibiting broad sensitivity and high specificity for scrub typhus infection.

similarly, inventor had further developed as a further embodiment of this invention, an improved method (PROCEDURE II) for the production of Karp r56, Kato r56 and Gilliam r56. Surprisingly, the final products prepared in accordance with this new method were produced in substantially higher concentration and purity and with less impurities and less aggregates as compared to the products prepared by the previous process (PROCEDURE I) disclosed herein. More specifically, the improved method (PROCEDURE II) is as follows:

Procedure II

1. Expression of r56: Plasmids carrying the insert were transformed into the expression host *E. coli* BL21. Recombinant *E. coli* expressing r56 were induced with isopropyl-beta-D-thiogalactopyranoside (IPTG) in the log phase and propagated in LB medium over night at 37° C. with shaking.

2. Purification of r56 polypeptide: The r56 polypeptides were expressed as inclusion bodies (IB) in *E. coli* BL21. Cell pellets were re-suspended in buffer A (20 mM Tris-HCl, pH 8.0), containing 5 mM EDTA and 0.1 mM of phenylmethylsulfonyl fluoride (PMSF). The cells were disrupted by passing through microfluidizer three times and the cell extract was centrifuged at 8,000×g for 30 min. The pellets were extracted with 2 M urea in buffer A and dissolved in 8 M urea containing 10-20 mMDTT for 2.5 to 5 mg/ml of r56. After incubation at room temperature for at least 20 minutes, the sample solution was centrifuged at 8,000×g for 5 minutes. The clear supernatant (<1/10 of the column volume) was applied to size-exclusion columns TSK P3000SW (21.5 mm×50 cm)—tandem TSK P4000SW (21.5 mm×100 cm) column equilibrated with 8 M urea and 1 mM DTT in 20 mM Tris-Hcl, pH 7.8 (buffer B). Peak fractions containing the r56 polypeptide were pooled and loaded into the anion-exchange DEAE column (21.5 mm×30 cm). The bound r56 was eluted with a linear gradient of NaCl from 0 to 0.4 M in buffer B over 30-60 min at a flow rate of 5 ml/min.

3. Refolding of the Purified r56 Polypeptide:

Refolding of r56 in buffer B were achieved by sequential dialysis with 6 M urea, and 2 M urea in buffer A and finally with buffer A only. The peak fractions from the DEAE column were combined and dialyzed against 8 volumes of 6 M urea in buffer A for 30 minutes at 4 degrees Celsius (4 C.) followed with two changes of the dialysis solution and dialyzed for a total of an additional 60 minutes. The same procedure was repeated with 4 M and 2 M urea in buffer A, except 0.3 uM of oxidized form of glutathione was included in the 4M urea solution. The final dialysis was against buffer A with two initial changes of buffer for 30 min each, and finally over night at 4 C.

Protection Efficacy Data for (a) r56 (Karp Only), (b) r56 (Kato Only) and (c) a Mixture of r56 Karp, r56 Kato and r56 Gilliam, Challenged by Kato.

TABLE 5

Immunoprotection of Swiss Outbred CD1 Mice from *Orientia tsutsugamushi* Karp Strain with Kp r56 Vaccine using Freund's Incomplete Adjuvant and Alum + CpG.

| VACCINE | ADJUVANT | BOOST | PROTECTION | SEROLOGY |
|---|---|---|---|---|
| PBS | FIA | — | 38.5% | 0.10 ± 0.25 |
| PBS | FIA | Boost | 52.9% | 0.06 ± 0.06 |
| PBS | Alum-CpG | — | 41.2% | 0.12 ± 0.09 |
| PBS | Alum-CpG | Boost | 30.8% | 0.06 ± 0.07 |
| Kp r56 | FIA | — | 100% | 1.56 ± 0.15 |
| Kp r56 | FIA | Boost | 95% | 1.49 ± 0.08 |
| Kp r56 | Alum-CpG | — | 76.9% | 1.48 ± 0.08 |
| Kp r56 | Alum-CpG | Boost | 73.7% | 1.42 ± 0.12 |

FIA = Freund's Incomplete Adjuvant
IP challenge of Swiss outbred CD1 mice

TABLE 6

Dose Dependence of Immunoprotection of Swiss Outbred CD1 Mice from *Orientia tsutsugamushi* Kato Strain with Kato r56 Vaccine in the presence of Freund's Incomplete Adjuvant.

| VACCINE (KATO r56) | Protection |
|---|---|
| 0.0 ug | 0% |
| 0.8 ug | 14% |
| 2.5 ug | 43% |
| 8.0 ug | 43% |
| 25 ug | 57% |

IP Challenge of Swiss outbred CD1 mice

TABLE 7

Efficacy of the trivalent vaccine (KpKtGm r56) against homologous challenge of Kato strain.

| Challenge Strain of *O. tsutsugamushi* | Vaccinated Mice (#survived/total#) | Unvaccinated Mice (#survived/total#) |
|---|---|---|
| PBS | 7/7 | 7/7 |
| Kato (1,000 LD50; IP) | 4/7* | 0/7 |

*Time to death was increased slightly by vaccination when compared to unvaccinated (PBS injected) control mice. IP challenge of Swiss outbred CD1 mice.

The inventors have disclosed efficacy data which supports the used of one, two or all three antigens in a monovalent, bivalent and trivalent pharmaceutical composition, immunogenic composition and vaccine, respectively. One of ordinary skill in the art will readily recognize that DNA only approach, a protein only approach, or a prime-boost approach using DNA in the initial dose and protein in the following dose may be used for the vaccine.

It is contemplated by the inventor(s) that the following five (5) categories of bioactive substances, combinations thereof and their use are within the scope of this invention:

1. r56 Karp prepared by PROCEDURE I and II
2. r56 Karp prepared by PROCEDURE I and II in combination with r56 Kato prepared by PROCEDURE I and II
3. r56 Karp prepared by PROCEDURE I and II in combination with r56 Gilliam prepared by PROCEDURE I and II
4. rKarp prepared by PROCEDURE I and II, rKato prepared by PROCEDURE I and II, rGilliam prepared by PROCECURE I and II, and
5. Each of the categories (1-4) herein above in combination with other bioactive and pharmaceutically-acceptable.

REFERENCES

1. Amano, K., A. Tamuta, N. Ohashi, H. Urakami, S. Kaya, and K. Fukushi. 1987. Deficiency of peptidoglycan and lipopolysaccharide components in *Rickettsia tsutsugamushi*. Infect. Immun. 55:2290-2292.
2. Blanar, M. A., D. Kneller, A. J. Clark, A. E. Karu, F. E. Cohen, R. Langridge, and I. D. Kuntz. 1984. A model for the core structure of the *Escherichia coli* RecA protein. Cold Spring Harb. Symp. Quant. Biol. 49:507-511.
3. Bourgeois, A. L., J. G. Olson, R. C. Fang, J. Huang, C. L. Wang, L. Chow, D. Bechthold, D. T. Dennis, J. C. Coolbaugh, and E. Weiss. 1982. Humoral and cellular responses in scrub typhus patients reflecting primary infection and reinfection with *Rickettsia tsutsugamushi*. Am. J. Trop. Med. Hyg. 31:532-540.
4. Bozeman, F. M., and B. L. Elisberg. 1963. Serological diagnosis of scrub typhus by indirect immunofluorescence. Proc. Soc. Exp. Biol. Med. 112:568-573.
5. Brown, G. W., D. M. Robinson, D. L. Huxsoll, T. S. Ng, K. J. Lim, and G. Sannasey. 1976. Scrub typhus: a common cause of illness in indigenous populations. Trans. R. Soc. Trop. Med. Hyg. 70: 444-448.
6. Brown, G. W., J. P. Saunders, S. Singh, D. L. Huxsoll, and A. Shirai. 1978. Single dose doxycycline therapy for scrub typhus. Trans. R. Soc. Trop. Med. Hyg 72:412-416.
7. Chang W-H. 1995. Current status of *tsutsugamushi* disease in Korea. J. Korean Med. Sci. 10:227-238.
8. Ching, W. M., H. Wang, and G. A. Dasch. 1996. Identification of human antibody epitopes on the 47 kDa, 56 kDa, and 22 kDa protein antigens of *Orientia tsutsugamushi* with synthetic peptides. Amer. J. Trop. Med. Hyg. 55:300. Abstract # 608.
9. Cohen, F. E., R. M. Abarbanel, I. D. Kuntz, and R. J. Fletterick. 1983. Secondary structure assignment for $\alpha/\beta$ proteins by a combinatorial approach. Biochemistry 22:4894-4904.
10. Crum, J. W., S. Hanchalay, and C. Eamsila. 1980. Mew paper enzyme-linked immunosorbent technique compared with microimmunofluorescence for detection of human serum antibodies to *Rickettsia tsutsugamushi*. J. Clin. Microbiol. 11:584-588.
11. Dasch G. A., S. Halle, and L. Bourgeois. 1979. Sensitive microplate enzyme-linked immunosorbent assay for detection of antibodies against the scrub typhus *rickettsia*.
12. Dasch. G. A., D. Strickman, G. Watt, and C. Eamsila. 1996. Measuring genetic variability in *Orientia tsutsugamushi* by PCR/RFLP analysis: a new approach to questions about its epidemiology, evolution, and ecology, p. 79-84. In J. Kazar (ed.) Rickettsiae and Rickettsial Diseases. Vth International Symposium. Slovak Academy of Sciences, Bratislava.
13. Dohany A. L., A. Shirai, D. M. Robinson, S. Ram, and Z D. L. Huxsoll. 1978. Identification and antigenic typing of *Rickettsia tsutsugamushi* in naturally infected chiggers (Acarina: Trombiculidae) by direct immunofluorescence. Am. J. Trop. Med. Hyg. 27:1261-1264.
14. Furuya, Y., Y. Yoshida, T. Katayama, F. Kawamori, S. Yamamoto, N. Ohashi, A. Kamura, and A. Kawamura, Jr. 1991. Specific amplification of *Rickettsia tsutsugamushi* DNA from clinical specimen by polymerase chain reaction. J. Clin Microbiol. 29: 2628-2630.
15. Greenfield, N., and G. D. Fasman. 1969. Computed circular dichroism spectra for the evaluation of protein conformation. Biochemistry 10:4108-4116.
16. Hanson, B. 1985. Identification and partial characterization of *Rickettsia tsutsugamushi* major protein immunogens. Infect. Immun. 50:603-609.
17. Horinouchi, H., K. Murai, A. Okayama, Y. Nagatomo, N. Tachibana, and H. Tsubouchi. 1996. Genotypic identification of *Rickettsia tsutsugamushi* by restriction fragment length polymorphism analysis of DNA amplified by the polymerase chain reaction. Am. J. Trop. Med. Hyg. 54:647-651.
18. Kelly, D. J., G. A. Dasch, T. C. Chye, and T. M. Ho. 1994. Detection and characterization of *Rickettsia tsutsugamushi* (Rickettsiales: Rickettsiaceae) in infected *Leptotrombidium* (*Leptotrombidium*) *fletcheri* chiggers (Acari: Trombiculidae) with the polymerase chain reaction. J. Med. Entomol. 31:691-699.
19. Kelly, D. J., D. Marana, C. Stover, E. Oaks, and M. Carl. Detection of *Rickettsia tsutsugamushi* by gene amplification using polymerase chain reaction techniques. Ann. N. Y. Acad. Sci. 590:564-571.
20. Kelly, D. J., P. W. Wong, E. Gan, and G. E. Lewis, Jr. 1988. Comparative evaluation of the indirect immunoperoxidase test for the serodiagnosis of rickettsial disease. Am. J. Trop. Med. Hyg. 38:400-406.
21. Kim, I-S., S-Y. Seong, S-G. Woo, M-S. Choi, and W-H. Chang. 1993. High-level expression of a 56-kilodalton protein gene (bor56) of *Rickettsia tsutsugamushi* Boryong and its application to enzyme-linked immunosorbent assays. J. Clin. Microbiol. 31:598-605.
22. Kim, I-S., S-Y. Seong, S-G. Woo, M-S. Choi, and W-H. Chang. 1993. Rapid diagnosis of scrub typhus by a passive hem agglutination assay using recombinant 56-kilodalton polypeptide. J. CLin. Microbiol. 31:2057-2060.
23. Moree, M. F., and B. Hanson. 1992. Growth characteristics and proteins of plaque-purified strains of *Rickettsia tsutsugamushi*. Infect. Immun. 60:3405-3415.
24. Murata, M. Y. Yoshida, M. Osono, N. Ohashi, Oyanagi, H. Urakami, A. Tamura, S. Nogami, H. Tanaka, and A. Kawamura, Jr. 1986. Production and characterization of monoclonal strain-specific antibodies against prototype strains of *Rickettsia tsutsugamushi*. Microbiol. Immunol. 30:599-610.
25. Ohashi, N., Y. Koyama, H. Urakami, M. Fukuhara, A. Tamura, F. Kawamori, S. Yamamoto, S. Kasuya, and K. Yoshimura. 1996. Demonstration of antigenic and genotypic variation in *Orientia tsutsugamushi* which were isolated in Japan, and their -classification into type and subtype. Microbiol. Immunol. 40:627-638.
26. Ohashi, N., H. Nashimoto, H. Ikeda, and A. Tamura. 1992. Diversity of immunodominant 56-kDa type-specific antigen (TSA) of *Rickettsia tsutsugamushi*. Sequence and comparative analyses of the genes encoding TSA homologues from four antigenic variants. J. Biol. Chem 267: 12728-12735.

27. Ohashi, N., A. Tamura, M. Ohta, and K. Hayashi. 1989. Purification and partial characterization of a type-specific antigen of *Rickettsia tsutsugamushi*. Infect. Immun. 57:1427-1431.

28. Ohashi, N., A. Tamura, H. Sakurai, and T. Suto. 1988. Immunoblotting analysis of anti-rickettsial antibodies produced in patients of *tsutsugamushi* disease. Microbiol. Immunol. 32:1085-1092.

29. Ohashi, N., A. Tamura, H. Sakurai, and S. Yamamoto. 1990. Characterization of a new antigenic type, Kuroki, of *Rickettsia tsutsugamushi* isolated from a patient in Japan. J. Clin. Microbiol. 28:2111-2113.

30. Robinson, D. M., G. Brown, E. Gan, and D. L. Huxsoll. 1976. Adaptation of a microimmunofluorescence test to the study of human *Rickettsia tsutsugamushi* antibody. Am. J. Trop. Med. Hyg. 25:900-905.

31. Saunders, J. P., G. W. Brown, A. Shirai, and D. L. Huxsoll. 1980. The longevity of antibody to *Rickettsia tsutsugamushi* in patients with confirmed scrub typhus. Trans. Roy. Soc. Trop. Med. Hyg. 74:253-257.

32. Shirai, A., D. M. Robinson, G. W. Brown, E. Gan, and D. L. Huxsoll. 1979. Antigenic analysis by direct immunofluorescence of 114 isolates of *Rickettsia tsutsugamushi* recovered from febrile patients in rural Malaysia. Japan J Med Sci Biol 32:337-344.

33. Silverman, D. J., and C. L. Wisseman, Jr. 1978. Comparative ultrastructural study on the cell envelopes of *Rickettsia prowazekii, Rickettsia rickettsii*, and *Rickettsia tsutsugamushi*. Infect. Immun. 21(3):1020-1023.

34. Stover, C. K., D. P. Marana, J. M. Carter, B. A. Roe, E. Mardis, and E. V. Oaks. 1990. The 56-kilodalton major protein antigen of *Rickettsia tsutsugamushi*: molecular cloning and sequence analysis of the sta56 gene and precise identification of a strain-specific epitope. Infect. Immun. 58(7):2076-2084.

35. Studier, F. W., and B. A. Moffatt. 1986. Use of bacteriophage T7 RNA polymerase to direct selective high-level expression of cloned genes. J. Mol. Biol. 189:113-130.

36. Sugita, Y., T. Nagatani, K Okuda, Y. Yoshida, and H. Nakajima. 1992. Diagnosis of typhus infection with *Rickettsia tsutsugamushi* by polymerase chain reaction. J. Med. Microbiol. 37:357-360.

37. Suto, T. 1980. Rapid serological diagnosis of *tsutsugamushi* disease employing the immuno-peroxidase reaction with cell cultured rickettsia. Clin. Virol. 8:42538. Suwanabun, N., C. Chouriyagune, C. Eamsila, P. Watcharapichat, G. A. Dasch, R. S. Howard, and D. J. Kelly. 1997. Evaluation of an enzyme-linked immunosorbent assay in Thai scrub typhus patients. Am. J. Trop. Med. Hyg. 56:38-43

39. Tamura, A., N. Ohashi, Y. Koyama, M. Fukuhara, F. Kawamori, M. Otsuru, P-F. Wu, and S-Y. Lin. 1997. Characterization of *Orientia tsutsugamushi* isolated in Taiwan by immunofluorescence and restriction fragment length polymorphism analyses. FEMS Microbiol. Lett. 150:224-231.

40. Urakami, H., S. Yamamoto, T. Tsuruhara, N. Ohashi, and A. Tamura. 1989. Serodiagnosis of scrub typhus with antigens immobilized on nitrocellulose sheet. J. Clin. Microbiol. 27:1841'-1846.

41. Weddle, J. R., T. C. Chan, K. Thompson, H. Paxton, D. J. Kelly, G. Dasch, and D. Strickman. 1995. Effectiveness of a dot-blot immunoassay of anti-*Rickettsia tsutsugamushi* antibodies for serologic analysis of scrub typhus. Am. J. Trop. Med. Hyg. 53:43-46.

42. Yamamoto, S., N. Kawabata, A. Tamura, H. Urakami, N. Ohashi, M. Murata, Y. Yoshida, and A. Kawamura, Jr. 1986. Immunological properties of *Rickettsia tsutsugamushi*, Kawasaki strain, isolated from a patient in Kyushu. Microbiol. Immuno. 30:611-620.

43. Yamamoto, S., and Y. Minamishima. 1982. Serodiagnosis of *tsutsugamushi* fever (scrub typhus) by the indirect immunoperoxidase technique. J. Clin. Microbiol. 15:1128-1132.

Obviously, many modifications and variations of the present invention are possible in light of the above teachings. It is therefore to be understood that, within the scope of the appended claims, the invention may be practiced otherwise than as specifically described. It is contemplated that this invention can be used to develop and/or augment vaccine therapy, prophylactic and therapeutic treatments for other diseases caused by facultative intracellular pathogens and/or agents such as a virus, bacteria, fungus, venom, pollen, protozoal, and mixtures thereof.

What is claimed is:

1. A vaccine containing a recombinant polypeptide comprising the amino acid sequence set forth in SEQ ID NO.: 1 and the amino acid sequence set forth in SEQ ID NO.: 4.

2. A vaccine containing a recombinant polypeptide comprising the amino acid sequence set forth in SEQ ID NO.: 1 and the amino acid sequence set forth in SEQ ID NO.: 5.

* * * * *